US007449428B2

(12) United States Patent
Peng et al.

(10) Patent No.: US 7,449,428 B2
(45) Date of Patent: Nov. 11, 2008

(54) CONTROL OF WEED WITH A FUNGAL PATHOGEN

(75) Inventors: Gary Peng, Saskatoon (CA); Kelly N. Byer, Saskatoon (CA)

(73) Assignee: Her Majesty The Queen in Right of Canada as represented by the Minister of Agriculture and Agri-Food Saskatoon Research Centre, Saskatoon (CA)

( * ) Notice: Subject to any disclaimer, the term of this patent is extended or adjusted under 35 U.S.C. 154(b) by 287 days.

(21) Appl. No.: 10/476,219

(22) PCT Filed: Apr. 30, 2002

(86) PCT No.: PCT/CA02/00637

§ 371 (c)(1),
(2), (4) Date: Aug. 27, 2004

(87) PCT Pub. No.: WO02/087343

PCT Pub. Date: Nov. 7, 2002

(65) Prior Publication Data

US 2005/0054530 A1   Mar. 10, 2005

(30) Foreign Application Priority Data

Apr. 30, 2001   (CA)   ................... 2345503
Sep. 26, 2001   (CA)   ................... 2357889

(51) Int. Cl.
*A01N 63/00* (2006.01)
(52) U.S. Cl. ................... 504/117; 424/93.5; 504/118
(58) Field of Classification Search ................ 504/117; 435/254.1, 256.8, 911
See application file for complete search history.

(56) References Cited

U.S. PATENT DOCUMENTS 4,606,751 A      8/1986   Van Dyke et al.
4,775,405 A *   10/1988   Caulder et al. .............. 504/117
5,635,444 A      6/1997   Walker et al.
6,265,347 B1 *   7/2001   Chandramohan et al. ... 504/117

FOREIGN PATENT DOCUMENTS

WO       WO 98 08389 A     3/1998

OTHER PUBLICATIONS

Murakami et al. "Analysis of Host Species Specificity of Magnaporthe grisea Toward Wheat Using a Genetic Cross Between Isolates from Wheat and Foxtail Millet". Phytopathology. 90(10)1060-1067. 2000.*
Kulkarni (Comparitive studies of four Isolates of Pircularia setariae Nishikado from setaria species in India (Mycopathologia 1969).*
Nukina 1987 Agric. Biol. Chem., 51(9): 2625-2628.*
Nukina et al 1991 Agric. Biol. Chem., 55(7): 1899-1900.*

Marta C. Filippi, et al., "Relationship Between Panicle Blast Severity and Mineral Nutrient Content of Plant Tissue in Upland Rice," Journal of Plant Nutrition, 1998, pp. 1577-1587, vol. 21, No. 8.
I. J. Graham-Bryce, "Crop protection: a consideration of the effectiveness and disadvantages of current methods and of the scope for improvement,"Phil. Trans. R. Soc. Lond., 1977, pp. 163-179, vol. 281.
M. P Graves, et al., "Formulation of microbial herbicides," Aspects of Applied Biology, 2000, pp. 171-178, vol. 57.
S. Green, et al., "Effects of Leaf Maturity, Infection Site, and Application Rate of Alternaria cirsinoxia Conidia on Infection of Canada Thistle (Cirsium arvense)," Biological Control, 2000, pp. 167-174, vol. 19.
Raj Grover, "Airborne off-target losses and deposition characteristics from a self-propelled, high speed and high clearance ground sprayer," Canadian Journal of Plant Science, 1997, pp. 493-500, vol. 77.
G. S. Hartley, et al., "Reflection of Water Drops from Surfaces," Surface Phenomena in Chemistry and Biology, 1958, pp. 214-223, Pergamon Press, New York, London, Paris, Los Angeles.
Chester M. Himel, "Pesticide Sources to the Soil and Principles of Spray Physics," Pesticides in the Soil Environment: Processes, Impacts, and Modeling, 1990, pp. 7-49, Chapter 2.
E. F. Guha,et al., "Studies on the identity and control of of stilbaceous mold in gas-purifying sponge," Phytopathology, 1945, p. 655, vol. 35.
J. G. Horsfall, "An improved grading system for measuring plant disease," Phytopathology, 1945, p. 655, vol. 35.
F. L. Howard, et al., Susceptibility of Logan and Florida Belle beans to Fusarium yellows, Phytopathology, 1945, p. 655, vol. 35.
R. C. Jones, "Factors influencing the development of resistant sporangia on Allomycas arbusculus", Phytopathology, 1945, p. 655, vol. 35.
Keith A. Jones, "Appendix II: Spray Application Criteria," Formulation of Microbial BioPesticides, 1998, pp. 367-375 (Library of Congress Publication Card No. 9870274).
Keith A. Jones, et al., "Technology of Formulation and Application," Formulation of Microbial Biopesticides, 1998, pp. 8-30 (Library of Congress Publication Card No. 98-70274).

(Continued)

*Primary Examiner*—David H Kruse
(74) *Attorney, Agent, or Firm*—Sughrue Mion, PLLC

(57) ABSTRACT

The present invention provides an isolated biocontrol agent, which is a strain of *Pyricularia setariae*. The present invention also relates to a biocontrol composition comprising at least one fungal biocontrol agent, which is a strain of *Pyricularia setariae*. Examples of the biocontrol agent of the present invention include *Pyricularia setariae* 94-409A (IDAC 190701-1), *Pyricularia setariae* 01-069A (IDAC 290102-01), and *Pyricularia setariae* 01-071A (IDAC 290102-02). Preferably, the biocontrol composition comprises an acceptable medium such as a liquid culture medium or a solid culture medium. The biocontrol agent or biocontrol composition may be used to suppress the growth of a weeds such as green foxtail (*Setaria viridis* [L.] Beauv.).

49 Claims, 7 Drawing Sheets

OTHER PUBLICATIONS

Moritz Knoche, "Effect of droplet size and carrier volume on performance of foliage-applied herbicides," Crop Protection, 1994, pp. 163-178, vol. 13, No. 3.

Ebbe Nordbo, et al., "Effects of Wind Direction, Wind Speed and Travel Speed on Spray Deposition," Pesticide Science, 1993, pp. 33-41, vol. 38.

Donald L. Reichard, "Drop Formation and Impaction on the Plant," Weed Technology, 1988, pp. 82-87, vol. 2.

R. G. Richardson, "Effect of drop trajectory on spray deposits on crop and weeds," Plant Protection Quarterly, 1987, pp. 108-111, vol. 2, No. 3.

D. B. Smith, et al., "Machinery and Factors that Affect the Application of Pathogens," Microbial Control of Pests and Plant Diseases, 1981, pp. 635-653, Chapter 35.

John J. Spillman, "Spray Impaction, Retention and Adhesion: an Introduction to Basic Characteristics," Pesticide Science, 1984, pp. 97-106, vol. 15.

Thomas M. Wolf, et al., "Calibration of Greenhouse Spray Chambers—The Importance of Dynamic Nozzle Patternation," Weed Technology, 1997, pp. 428-435, vol. 11.

Thomas M. Wolf, et al., "Optimizing postemergence herbicide deposition and efficacy through application variables in no-till systems," Weed Science, 2000, pp. 761-768, vol. 48.

Ziva Amsellem, et al., "Long-term dry preservation of viable mycelia of two mycoherbicidal organisms," Crop Protection, 1999, pp. 643-649, vol. 18.

S. R. Colby, "Calculating Synergistic and Antagnonistic Responses of Herbicide Combinations," Weeds, 1966, pp. 20-22, Scientific Article No. A 1271 of the Maryland Agricultural Experiment Station.

A. P. Gaikwad, et al., "A comparative study on Pyricularia species," Journal of Maharashtra Agricultural Universities, 1987, pp. 134-135, vol. 12., No. 1.

K. Sivaprakasam, et al., "Note on the Effect of Fungicides on the Control of Finger Millet Blast," Indian Journal of Agricultural Sciences, 1974, vol. 44, No. 4, (abstract).

A. K. Jain, "Multiple disease resistance in foxtail millet," Annals of Plant Protection Sceiences, 2000. pp. 268-270, vol. 8, No. 2.

B. S. Pall, et al., "Chemical Control of Ragi Eleusine-Coracana Blast," Pestisides, 1985, pp. 54 & 60, vol. 19. No. 5.

B. S. Pall, et al., "Screening early varieties of ragi (Eleusine coracana (L) Gaertn.) ragimillet against blast disease incited by Pyricularia setariae," Food Farming and Agriculture, 1979, pp. 56-57, vol. 12, No. 3.

A. K. Jain, et al., "Stability of resistance to blast in foxtail millet," Mysore Journal of Agricultural Science, 1991, pp. 221-223, vol. 25, No. 2.

D'Souza T. F., et al., "Varietal resistance of Setaria (Setaria Italica) to blast caused by Pryicularia Setariae," Indian Phytopathology, 1984, pp. 605-607, vol. 37. No. 4.

E. Nitzanie, et al., "Foliar Disease of Purple Nutsedge in Israel as Potential Biocontrol Agent," Phytoparasitica, 1990, pp. 240-241, vol. 18, No. 3, (abstract).

* cited by examiner

CONTROL OF WEED WITH A FUNGAL PATHOGEN

This Application is a 371 of PCT/CA02/00637, filed Apr. 30, 2002; the disclosure of which is incorporated herein by reference.

The invention relates to biocontrol agents for suppressing weed growth. More specifically the present invention relates to fungal biocontrol agents for suppression of weed growth.

BACKGROUND OF THE INVENTION

Control of weeds is an important aspect of crop management. Due to several undesirable properties associated with the use of chemical herbicides, alternative weed control practices, including the use of biological herbicides, are desired. For example, rising economic, environmental and social costs associated with agricultural inputs, spray drift, pesticide residues, government legislation for reduced pesticide use, along with the development of herbicide resistance in weeds, make biocontrol agents attractive strategies for weed control.

Biological control of weeds with microorganisms (bioherbicides), preferably involves the production and application of a weed-specific pathogen to a target weed. The weed specific pathogen is typically a fungus or bacterial pathogen that inhibits or suppresses root, shoot or both root and shoot growth, development, or both growth and development, thereby reducing weed competition. The development of biological crop protection products (bioherbicides) for economically important weed problems in agricultural field crops may help to facilitate harvests, secure yields, and protect the environment. Biological control provides an additional tool to complement an integrated weed management system and helps sustainable agricultural systems by maintaining the ecosystem balance through the preservation of plant and microbial diversity in the field.

There are several documents disclosing the use of fungi as biocontrol agents. For example, U.S. Pat. No. 5,993,802 teaches methods for suppressing the growth of *Calamagrostis canadensis* using an isolate of a low temperature basidiomycete fungus, *Coprinus psychromorbidus*. U.S. Pat. No. 5,472,690 teaches of a mycoherbicide (including at least one or both of *Fusarium nivalis* and *Colletotrichum calamagrostidis*) effective in the control of *Calamagrostis canadensis* and/or related grasses. The control of crabgrass using fungi is disclosed in U.S. Pat. No. 5,952,264, using the fungus *Cochliobolus intermedius*, and U.S. Pat. No. 5,635,444 using a fungus selected from the genus *Curvularia*. U.S. Pat. No. 5,747,029, teaches the control of sicklepod weeds using the fungus *Myrothecium verrucaria*. The control of nutsedge weeds using the fungus *Dactylaria higginsii* is disclosed in WO 98/08389. U.S. Pat. No. 4,606,751 teaches the biocontrol of Johnson grass using *Bipolaris sorghicola* spores that are suspended in a solution of water and surfactant, and sprayed onto a field in which the weed is growing.

Annual grassy weeds such as *Setaria viridis* (L.) Beauv. (commonly known as green foxtail, pigeongrass, wild millet, green bristlegrass, and bottlegrass) develop dense competitive stands and have heavy seed production in spring sown crops. Green foxtail is a principal weed of corn, soybean, cereals, flax, canola, sugar beets, and pastures. The amount of damage to the crop depends on the density of the stand, time of emergence, and length of time the weed and crop are competing. Weed surveys for herbicide-resistant green foxtail have revealed that many of these plants exhibit some degree of herbicide resistance (Beckie, H. J., A. Legere, A. G. Thomas, L. T. Juras, and M. D. Devine. 1996 Survey of Herbicide-Resistant Wild Oat and Green Foxtail in Saskatchewan: Interim Report AAFC Report, 22 pp.). Therefore, biocontrol of these plants is highly desirable. However, at present for most of these weeds there are no known satisfactory biocontrol agents for control of green foxtail.

An important aspect in the development of a successful biological control agent is an effective delivery system. For biocontrol agents delivered onto target weeds by spraying, it is common for the erect top leaf to survive the attack due to the poor retention of the biocontrol agent on this portion of the plant. Thus, new methods of applying biocontrol agents are desired in the art. Further, traditional application methods such as run-off spraying are generally not suitable for treatment of large areas and thus there is a need in the art for methods to reduce the application volumes of biocontrol agents without reducing the efficacy of the biocontrol agent on the target weeds. To date, variable efficacy has been observed with biopesticide agents at reduced application volumes (Jones 1994, Smith and Bouse, 1981)

Previous attempts to control green foxtail weeds with biocontrol compositions have been relatively poor. In particular, it was noted in other studies that the top leaf of green foxtail consistently exhibited the least amount of disease development following biocontrol application, and reduced spray retention is speculated as a cause because of the erect leaf architecture of green foxtail weeds. Further, the surviving leaf often contributes to regrowth from the apical meristem, reducing the effectivity of the biocontrol agent. Other factors, such as but not limited to age (Green and Bailey 2000) and mineral nutrient content (Filippi and Prabhu 1998) of the leaves, may affect the susceptibility of green foxtail weeds to fungal pathogens.

In field crops, application volumes over 600 L/ha are considered high (Matthews, 1992), and the trend is generally toward volume reduction. In previous experiments, when applied at volumes between 100 to 800 L/ha, the agent 94-409A showed significantly lower efficacy in comparison to the runoff airbrush spray using the same spore concentration. Commonly the erect top leaf developed little disease and survived the attack. It is believed that the poorer efficacy is related to a lower amount of fungal propagules received and retained on the plant It is an object of the present invention to overcome drawbacks of the prior art.

The above object is met by a combination of the features of the main claims. The sub claims disclose further advantageous embodiments of the invention.

SUMMARY OF THE INVENTION

The invention relates to biocontrol agents for suppressing weed growth. More specifically, the present invention relates to fungal biocontrol agents for suppression of weed growth.

The present invention provides an isolated fungal biocontrol agent, which is a strain of *Pyricularia setariae*. In a preferred embodiment, the present invention provides an isolated fungal biocontrol agent, which is *Pyricularia setaniae* 94-409A (International Depositary Authority of Canada (IDAC) 190701-1; deposited on Jul. 19, 2001), *Pyricularia setariae* 01-069A (IDAC 290102-01, deposited on Jan. 29, 2002), and *Pyricularia setariae* 01-071A (IDAC 290102-02, deposited on Jan. 29, 2002), which exhibit weed suppressive activity. Also provided by the present invention is the use of the above biocontrol agents for controlling or suppressing the growth of foxtail weeds.

According to another aspect, the present invention provides a method for suppressing weed growth by applying an isolated biocontrol agent, which is a strain of *Pyricularia setariae* to a weed. In a preferred embodiment, the present invention provides a method for suppressing weed growth comprising applying *Pyricularia setariae* 94-409A (IDAC 190701-1), *Pyricularia setariae* 01-069A (IDAC 290102-01), *Pyricularia setariae* 01-071A (IDAC 290102-02), or a mixture thereof, to a weed. Preferably, the weed is green, yellow or giant foxtail (*Setaria viridis* [L.] Beauv., *S. glauca*, or *S. faberi*, respectively).

According to a further aspect, the present invention provides a biocontrol composition comprising at least one isolated fungal biocontrol agent, which is a strain of *Pyricularia setariae*, and a suitable medium. In a preferred embodiment, the present invention provides a biocontrol composition comprising *Pyricularia setariae* 94-409A (IDAC 190701-1), *Pyricularia setariae* 01-069A (IDAC 290102-01), or *Pyricularia setariae* 01-071A (IDAC 290102-02), or a mixture thereof, and a suitable medium. The suitable medium medium may comprise a liquid culture medium, a solid culture medium or a combination thereof. Preferably, the suitable medium is a liquid culture medium.

According to another aspect, the present invention provides a biocontrol composition comprising at least one isolated fungal biocontrol agent, which is a stain of *Pyricularia setariae*; and an herbicide. In a preferred embodiment, the present invention provides a biocontrol composition comprising *Pyricularia setariae* 94-409A (IDAC 190701-1), *Pyricularia setariae* 01-069A (IDAC 290102-01), or *Pyricularia setariae* 01-071A (IDAC 290102-02), or a mixture thereof, and an herbicide.

According to another aspect, the present invention provides a synergisitc biocontrol composition comprising a synergistic amount of at least one isolated fungal biocontrol agent, which is a strain of *Pyricularia setariae*; and a synergistic amount of an herbicide. In a preferred embodiment, the present invention provides a synergisitc biocontrol composition comprising a synergistic amount of *Pyricularia setariae* 94-409A (IDAC 190701-1), *Pyricularia setariae* 01-069A (IDAC 290102-01), or *Pyricularia setariae* 01-071A (IDAC 290102-02), or a mixture thereof, and a synergistic amount of an herbicide.

The present invention also provides the use of the above-indicated compositions for controlling or suppressing the growth of foxtail weeds. Preferably, the weed is green, yellow or giant foxtail (*Setaria viridis* [L.] Beauv., *S. glauca*, or *S. faberi*, respectively).

According to another aspect, the present invention provides a method for suppressing weed growth by applying the above-indicated compositions to a weed. Preferably, the weed is green, yellow or giant foxtail (*Setaria viridis* [L.] Beauv., *S. glauca*, or *S. faberi*, respectively).

According to another aspect, the present invention provides a method of suppressing weeds during crop growth comprising:
a) adding to soil an effective amount of a biocontrol composition comprising at least one isolated fungal biocontrol agent, which is a strain of *Pyricularia setariae*, formulated in an acceptable medium, to produce a treated soil;
b) planting crops in said treated soil; and
c) growing said crops.

Also according to the present invention, there is provided a method of suppressing weeds during crop growth comprising;
a) adding to soil an effective amount of a biocontrol composition comprising:
(i) at least one fungal biocontrol agent, which is a strain of *Pyricularia setariae*; and
(ii) an herbicide; formulated in an acceptable medium, to produce a treated soil;
b) planting crops in said treated soil; and
c) growing said crops.

Also according to the present invention, there is provided a method of suppressing weeds during crop growth comprising;
a) adding to soil an effective amount of a synergistic biocontrol composition comprising:
(i) a synergistic amount of at least one fungal biocontrol agent, which is a strain of *Pyricularia setariae*; and
(ii) a synergistic amount of an herbicide; formulated in an acceptable medium,
to produce a treated soil;
b) planting crops in said treated soil; and
c) growing said crops.

The present invention also provides a method of suppressing weeds during crop growth comprising:
a) spraying an area of plants with an effective amount of a biocontrol composition comprising at least one isolated fungal biocontrol agent, which is a strain of *Pyricularia setariae*, formulated in an acceptable medium; and
b) growing said plants.

The present invention further provides a method of suppressing weeds during crop growth comprising:
a) spraying an area of plants with an effective amount of a biocontrol composition comprising:
(i) at least one fungal biocontrol agent, which is a strain of *Pyricularia setariae*, and
(ii) an herbicide, formulated in an acceptable medium; and
b) growing said plants.

The present invention further provides a method of suppressing weeds during crop growth comprising:
a) spraying an area of plants with an effective amount of a synergistic biocontrol composition comprising:
(i) a synergistic amount of at least one fungal biocontrol agent, which is a strain of *Pyricularia setariae*, and
(ii) a synergistic amount of an herbicide, formulated in an acceptable medium; and
b) growing said plants.

In a preferred embodiment, the fungal biocontrol agent of the present invention is used in an amount of about $10^6$ to about $10^7$ spores per ml.

In a further aspect, the present invention provides a method of inhibiting foxtail weeds in a desired area, said method comprising spraying said desired area with between about 250 L/Ha to about 2000 L/Ha of a biocontrol composition comprising between about $10^6$ to about $10^7$ spores of at least one isolated fungal biocontrol agent, which is a strain of *Pyricularia setariae*.

In a preferred embodiment, the biocontrol agent used in the above-described methods is *Pyricularia setariae* 94-409A (IDAC 190701-1), *Pyricularia setariae* 01-069A (IDAC 290102-01), or *Pyricularia setariae* 01-071A (IDAC 290102-02), or a mixture thereof.

The biocontrol agent or biocontrol composition may be applied to weeds by any method known in the art, but is preferably applied by spraying, for example, but not limited to airbrush spraying or broadcast spraying. Broadcast application may be effected using a nozzle which enhances the reduction of the size of the droplets which are emitted during application of the biocontrol agent or composition as defined above. Preferably, the nozzles are XR TEEJET® extended range flat spray tips selected from the group consisting of XR8001, XR8002 and XR8004, which produce spray droplets having a volume median diameter (VMD) at 1 bar of about 280, about 350 and about 390 microns, respectively. However, other nozzles may also be employed to deliver the biocontrol agent or composition of the present invention.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 7 shows the synergistic effect of 94-409A with an herbicide.

DESCRIPTION OF PREFERRED EMBODIMENTS

Figure 1:
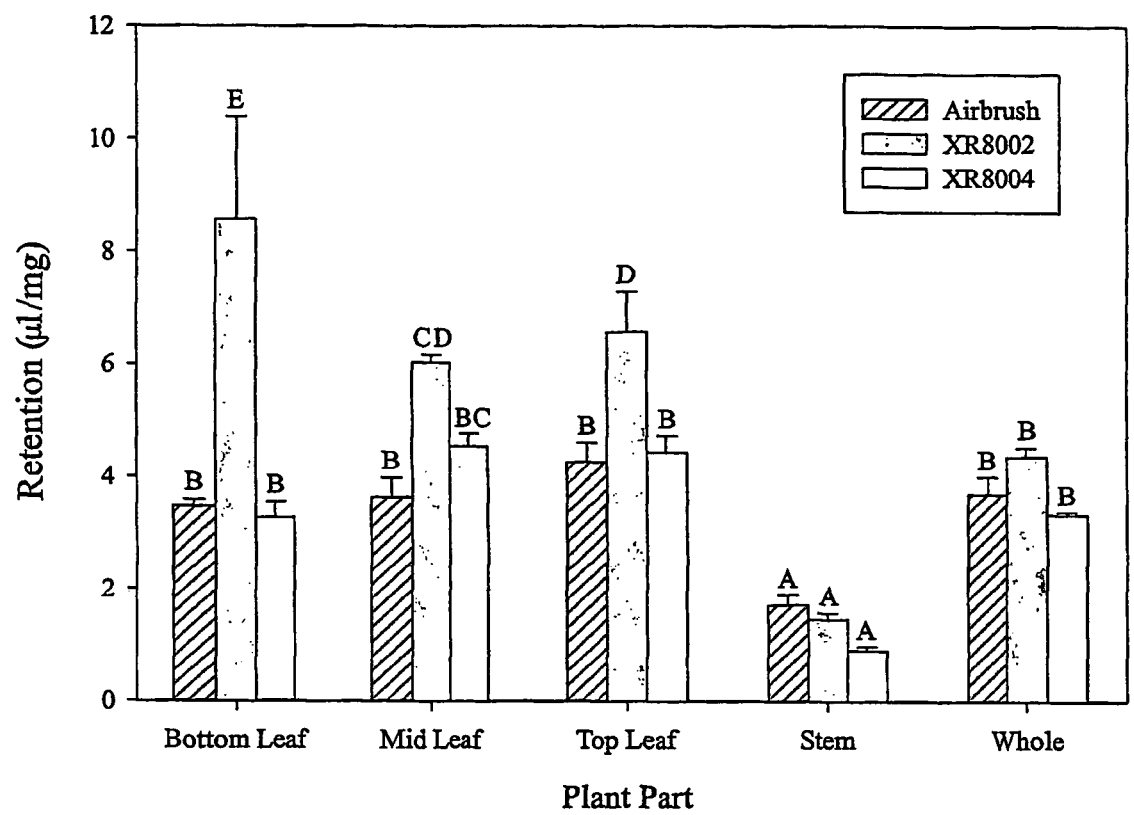
FIG. 1 shows retention volumes on different parts of green foxtail with airbrush sprayer (runoff) and broadcast sprayers (1,960 L/ha). The measurements were taken from different plant parts and expressed as ml/mg dry matter.

The invention relates to biocontrol agents for suppressing weed growth. More specifically the present invention relates to fungal biocontrol agents for suppression of weed growth.

The following description is of a preferred embodiment by way of example only and without limitation to the combination of features necessary for carrying the invention into effect.

The present invention provides a biocontrol agent comprising *Pyricularia setariae*. Examples of *Pyricularia setariae* strains that may be used as biocontrol agents, and that are not to be considered limiting in any manner, include *Pyricularia setariae* 94-409A (as deposited on Jul. 19, 2001 with the International Depositary Authority of Canada (IDAC), Bureau of Microbiology, Health Canada, 1015 Arlington Street, Winnipeg, Manitoba Canada R3E 3R2, under accession number IDAC 190701-1), *Pyricularia setariae* 01-069A (as deposited on Jan. 29, 2002 with the International Depositary Authority of Canada (IDAC), Bureau of Microbiology, Health Canada, 1015 Arlington Street, Winnipeg, Manitoba Canada R3E 3R2, under accession number IDAC 290102-01 and *Pyricularia setariae* 01-071A1 (as deposited on Jan. 29, 2002 with the International Depositary Authority of Canada (IDAC), Bureau of Microbiology, Health Canada, 1015 Arlington Street, Winnipeg, Manitoba Canada R3E 3R2, under accession number IDAC 290102-02), or a combination thereof.

The present invention also provides methods for controlling the growth of weeds using *Pyricularia setariae*. In a preferred embodiment, one or more than one *Pyricularia setariae* strain is used to control green foxtail (*Setaria viridis*) weeds.

Host range specificity was determined by testing biocontrol agent isolate 94-409A (IDAC 190701-1) for pathogenicity on at least one commercial cultivar of the following 26 crop species in a controlled greenhouse environment: *Triticum aestivum* (wheat), *Triticum durum* (durum wheat), *Hordeum vulgare* (barley), *Avena sativa* (oat), *Zea mays* (field and sweet corn), *Sorghum bicolor* (sorghum), *Oryza sativa* (rice), *Phalaris canariensis* (canarygrass), *Poa pratensis* (Kentucky Bluegrass), *Agrostis stolonifera* (creeping bentgrass), *Festuca rubra* (creeping red fescue), *Lolium perenne* (perennial ryegrass), *Panicum miliaceum* (proso millet), *Brassica Napus* (Agentile canola), *Brassica rapa* (Polish canola), *Brassica juncea* (oriental mustard), *Medicago sativa* (alfalfa), *Linum usitatissimum* (flax), *Carthamus tinctorius* (safflower), *Helianthus annus* (sunflower), *Lens culinaris* (lentil), *Pisum sativum* var. *arvense* (field pea), *Triflium pratense* (red clover), *Vicia faba* (faba bean), *Cicer arietinum* (chickpea), and *Glycine max* (soybean). Results indicate that 94-409A is very host specific, causing extensive damage only to green foxtail. However, other plants related to green foxtails may also be sensitive to 94-409A, for example but not limited to yellow foxtail (*S. glauca*) and giant foxtail (*S. faberi*).

By the term "biocontrol agent" it is meant a microorganism that suppresses the growth of, or kills, a target pest, for example, but not limited to a plant or a weed. More specifically, the biocontrol agents of the present invention may be used to suppress the growth of one or more target pests. Without wishing to be bound by theory, the biocontrol agent suppresses the growth of a target pest, for example, a plant or weed (i.e. exhibits weed suppressive activity), by interfering with the normal growth and development of the target plant or weed. For example, but not wishing to be limiting, the biocontrol agent may inhibit root growth, shoot growth, reduce biomass, inhibit seed production, reduce competitiveness of the target plant or weed for a crop's water and nutrients, or a combination thereof. Non-limiting examples of biocontrol agents of the present invention include:

*Pyricularia setariae* 94-409A (IDAC 190701-1; Jul. 19, 2001),

*Pyricularia setariae* 01-069A (IDAC 290102-01, Jan. 29, 2002),

*Pyricularia setariae* 01-71A1 (IDAC 290102-02, Jan. 29, 2002), or a combination thereof.

Furthermore, the biocontrol agent of the present invention may be used in conjunction with an herbicide, or an extract obtained from *Pyricularia setariae* may also be used in combination with an herbicide to control weed growth. Therefore, the present invention pertains to biocontrol compositions that comprise either a biocontrol agent, a biocontrol agent in a suitable medium, a biocontrol agent in combination with an herbicide, an extract obtained from *Pyricularia setariae*, an extract obtained from *Pyricularia setariae* in combination with an herbicide. A variety of herbicides may be used in conjunction with the biocontrol agent of the present invention. Examples of herbicides that may be used include but are not limited to ACC-ase inhibitors, ALS inhibitors, synthetic auxins, inhibitors of photosynthesis at PSII, inhibitors of EPSP, or inhibitors of glutamine synthetase.

As someone of skill in the art will understand, in order for the biocontrol agent of the present invention to be grown, cultured or used in accordance with the embodiments of the present invention, it is preferable that the biocontrol agent be grown in a suitable medium to produce a biocontrol composition or formulation. By the term "suitable medium" or "acceptable medium" it is meant any liquid, semi-liquid or solid substrate that allows one or more than one biocontrol agent of the present invention, for example but not limited to *Pyricularia setariae* 94-94-409A, 01-069A or 01-071A, to grow, or to remain viable, or both grow and remain viable. Thus, the present invention contemplates a biocontrol composition comprising fungal biocontrol agent *Pyricularia seariae* and a suitable medium. Preferably, the composition permits an effective amount of fungal biocontrol agent 94-409A to remain viable prior to, and after, being applied to a crop. More preferably, the composition permits fungal biocontrol agent *Pyricularia setariae* to remain viable for a period between about 1 day to about 1 month following application of the biocontrol composition of the present invention onto a plant, or soil.

The present invention provides a biocontrol agent, a biocontrol composition, an extract obtained from *Pyricularia setariae*, a combination of *Pyricularia setariae* and an herbicide, or a combination of an extract of *Pyricularia setariae* and an herbicide, for use in controlling weed growth. These agents, or compositions may be applied to plants, soil or both plants and soil. The composition maybe sprayed, or applied as a liquid to the leaves of a plant (e.g. see Examples 1-3), or as described in Example 4, the composition may be applied by drenching the soil containing weed seeds, or by coating the seeds with a spore or mycellial suspension then sowing into non-treated soils. Preferably, the biocontrol agent or composition is applied to plant foliage, for example the foliage of the target weed. Alternatively, the biocontrol agent or composition may be applied directly to soil, either before, during or after seeding a crop. The biocontrol agent may be applied by any method known in the art, for example, but not limited to spraying, pouring, dipping or the like. Preferably, the biocontrol composition of the present invention is applied by spraying.

Therefore, the present invention provides a method for the for the suppression of green foxtail, and related, weeds for example but not limited to yellow and giant foxtail (*S. faberi*) by applying fungal biocontrol agent *Pyricularia setariae* grown and formulated in a suitable composition. As someone of skill in the art will understand, the amount of the biocontrol composition required for suppression of green foxtail weeds may be dependent on the medium in which the fungal biocontrol agent is formulated and the method in which it is formulated. For example, but not wishing to be limiting, a formulation and medium which permits a greater percentage of the fungal agent to remain viable may require less biocontrol composition to suppress weed growth than does another formulation and medium in which biocontrol agent *Pyricularia setariae* is less viable. Further, the amount of a biocontrol composition required for suppression of weeds may be influenced by environmental factors such as but not limited to temperature, humidity, soil pH, and soil type.

Furthermore, the present invention provides a method for the for the suppression of green foxtail, and related, weeds for example but not limited to yellow and giant foxtail (*S. faberi*) by applying an extract obtained from the fungal biocontrol agent *Pyricularia setariae* (see Example 5). The extract may be applied to the plant or soil by spray, liquid drench, brushing, or as a rub for example a solid composition comprising an extract of the biocontrol agent.

Weed suppressive activity arising from *Pyricularia setariae*, is also observed on yellow and giant foxtail (*S. faberi*) when the biocontrol agent of the present invention is applied in combination with. an herbicide, (Examples 11, 12, Tables 12-14). A variety of herbicides may be used in conjunction with *Pyricularia setariae*, and include but are not limited to ACC-ase inhibitors, ALS inhibitors, synthetic auxins, inhibitors of photosynthesis at PSII, inhibitors of EPSP, or inhibitors of glutamine synthetase.

Referring now to Table 1, there is shown spray retention on plants by airbrush and broadcast application. The results shown in Table 1 suggest that the retention of spray on whole green foxtail plants generally increases with broadcast application volume. Also suggested by Table 1 is that spray retention on plants following broadcast application at a volume of about 1,960 L/ha produces a similar level to that of airbrush spraying. Thus, the present invention contemplates airbrush and broadcast application of fungal biocontrol agent *Pyricularia setariae*, or a biocontrol composition comprising biocontrol agent *Pyricularia setariae*. However, application of biocontrol agent *Pyricularia setariae* or a biocontrol composition comprising *Pyricularia setariae* is not limited to airbrush and broadcast application. For example, the biocontrol composition may be manually atomized using a hand pump spray, broadcast sprayed, applied as a liquid, for example through a hose or liquid applicator, or painted as required.

TABLE 1

Spray retention achieved by airbrush and broadcast applications at different volumes on green foxtail.

| Volumes | Airbrush | | Broadcast | | | | |
|---|---|---|---|---|---|---|---|
| Application Volume (L/ha) | 3 ml/pot* | 171 | 474 | 477 | 885 | 1187 | 1960 |
| Retention Volume (µl/plant) | 25.8 | 3.2 | 9.8 | 7.4 | 11.2 | 18.3 | 26.4 |

*Application volume resulting in runoff on 8 plants at the 3-leaf stage.

Referring now to FIG. 1, there is shown the results of spray retention on different plant parts following airbrush or broadcast application using nozzles that vary the droplet size of the spray. As shown by FIG. 1, spray retention is slightly higher on leaves than on the stems of plants when spray retention is measured on a dry matter basis.

Any spray nozzle may be used for the application of the biocontrol agent of the present invention. The results shown in FIG. 1 also suggest that broadcast application of the biocontrol composition of the present invention with the XR 8002 nozzle results in greater retention of spray on whole plants and leaves compared to broadcast application using a XR 8004 nozzle or by airbrush spraying. Without wishing to be bound by theory, smaller spray droplets may be better retained on plant leaves than are larger droplets. Thus modulation of the spray droplet size during application of the fungal biocontrol agent or composition of the present invention may enhance retention of the biocontrol control agent on target weeds.

Effects of Droplet Size and Travel Speed on Retention Efficiency of *Pyricularia Setariae*

Figure 2:
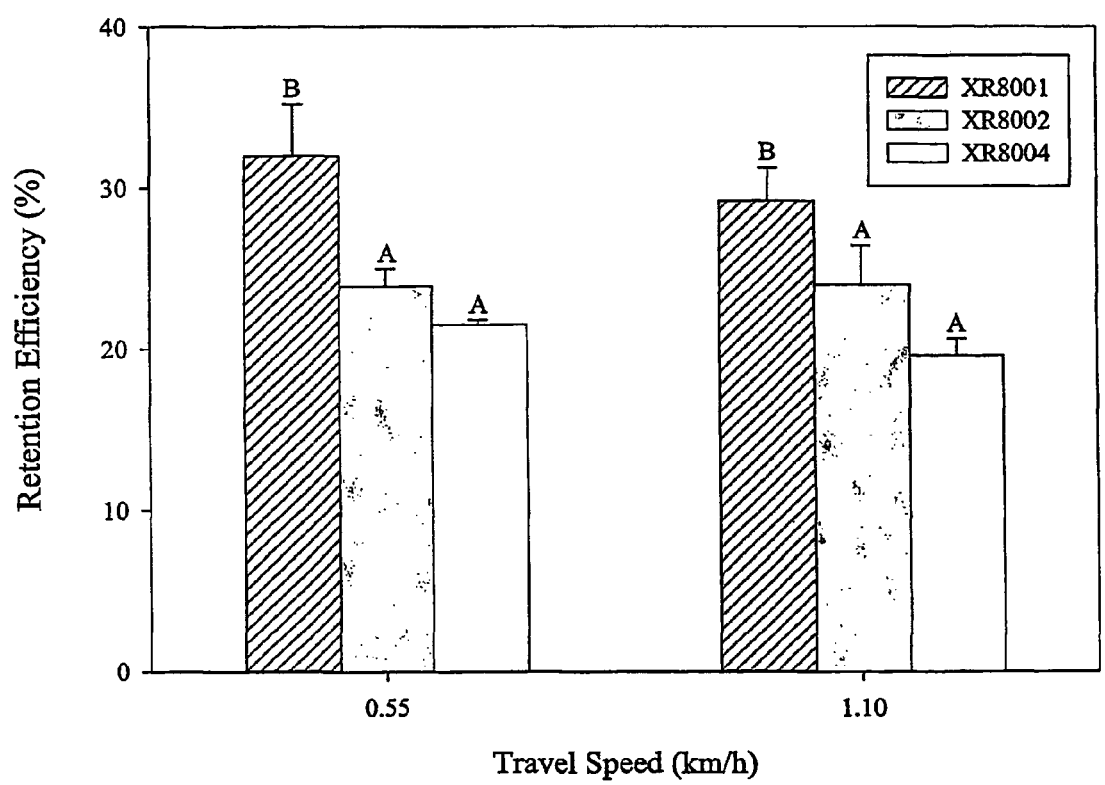
FIG. 2 shows the effect of spray droplet size and travel speed on the retention efficiency of spray on treated plants.

Retention efficiency is a term comparing the amount of a biocontrol agent on a plant following application relative to total application volume delivered. Referring now to FIG. 2, there is graphically depicted the retention efficiency of spray following broadcast application using nozzles XR 8001, XR 8002 and XR 8004 and using spray application speeds of 0.5 and 1.1 km per hour. Nozzles XR 8001, XR 8002 and XR 8004 produce progressively greater size droplets. The results demonstrate that a wide range of droplet sizes, and travell speeds are effective in applying the biocontrol agent of the present invention.

The application of smaller droplets result in a relatively higher proportion of spray being retained on the target weed. For example, but not wishing to be limiting, broadcast application of a biocontrol composition using a small droplet size nozzle (XR8001) results in greater retention efficiency of the biocontrol composition on plants than do larger droplet size nozzles XR8002 and XR8004 under the specific conditions under which the three nozzles were tested Also suggested by the results shown in FIG. 2 is that the travel speed of the droplets has little effect on the retention efficiency of the biocontrol composition and thus the fungal biocontrol compositions of the present invention may be applied in a wide range of droplet sizes and travel speeds. Preferably, the droplet sizes are small, for example in about the order of the droplets produced by a XR8001 nozzle. Further, it is preferable that the travel speeds of the droplets are in the range of about 0.4 km per hour to about 2 km per hour, more preferably between 0.55 and 1.10 km per hour. As would be evident to someone of skill in the art, travel speeds outside this range also may be used in accordance with the method of the present invention, but that the travel speed and droplet size should not be such that physical damage occurs to plants.

Retention and Biocontrol Efficacy of *Pyricularia setariae*

Figure 3:
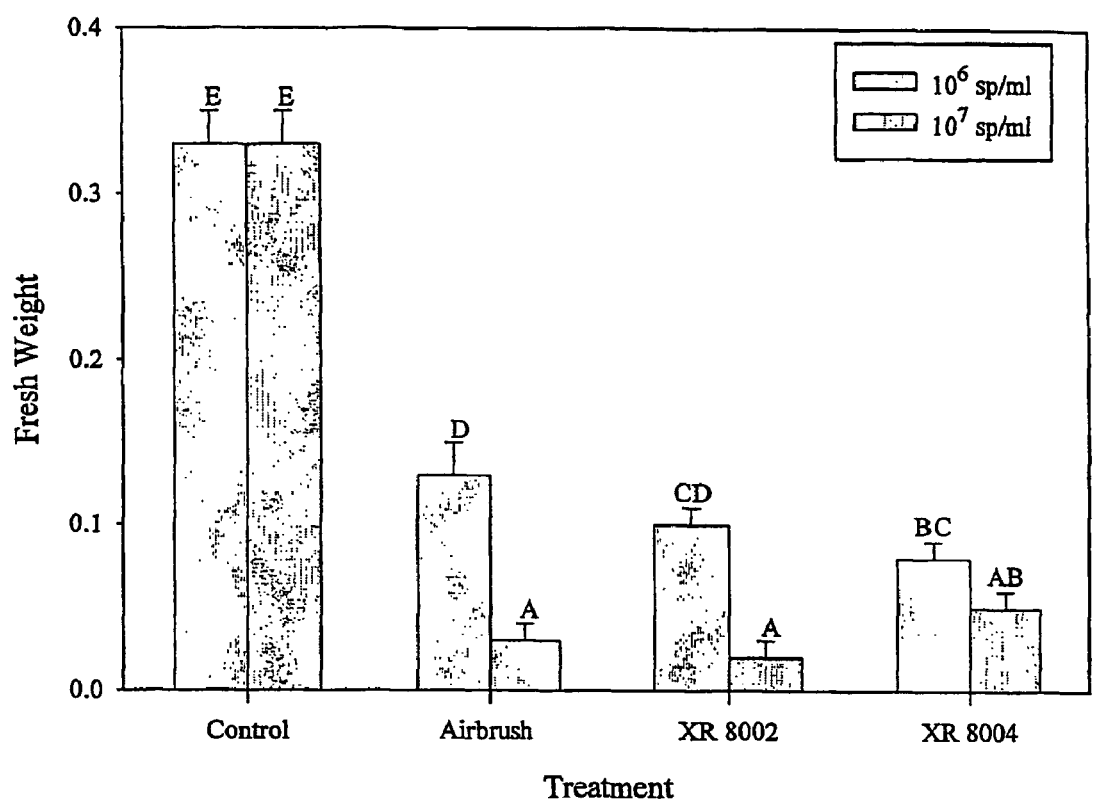
FIG. 3 shows the effect of application method, spore concentration, and droplet size on the efficacy of 94-409A as a biocontrol agent on green foxtail weeds.

Referring now to FIG. 3, there is shown the effect of application method, spore concentration and droplet size on the efficacy of fungal biocontrol agent, for example but not limited to *Pyricularia setariae* 94-409A on green foxtail. These results demonstrate that a wide range of spore concentrations may be effectively applied. Application of between about $10^6$ and about $10^7$ spores/ml of fungal biocontrol agent 94-409A onto the foliage of green foxtail weeds reduces the weight of the weeds, regardless of the method used to apply the composition. However, application of greater than or less than the spore concentration of between about about $10^6$ and about $10^7$ spores/ml may also be effective.

The results shown in FIG. 3 also suggest that fungal isolate 94-409A may be applied to green foxtail weeds by a variety of application methods, such as, but not limited to by airbrush, or broadcast spraying. Further, broadcast spraying of the biocontrol composition of the present invention in an amount of about 2000 L/ha, there was little difference between the two application methods (data not shown). At higher spore concentrations, there was no significant difference between application treatments, and the average plant fresh weight was reduced by about 85% to about 91% compared to the control. At lower doses the XR8004 nozzle appeared to be slightly more effective than the airbrush spray, but was comparable to the XR8002.

The biocontrol composition of the present invention may be applied at a concentration of spores sufficient to result in a desired amount of weed control activity, for example, which is not to be considered limiting, form between about $10^6$ and about $10^7$ spores/ml of fungal biocontrol agent *Pyricularia setariae*.

As described in more detail in Example 5, the biocontrol agent of the present invention may also be applied by applying homogenized mycellium in an appropriate medium.

Figure 6:
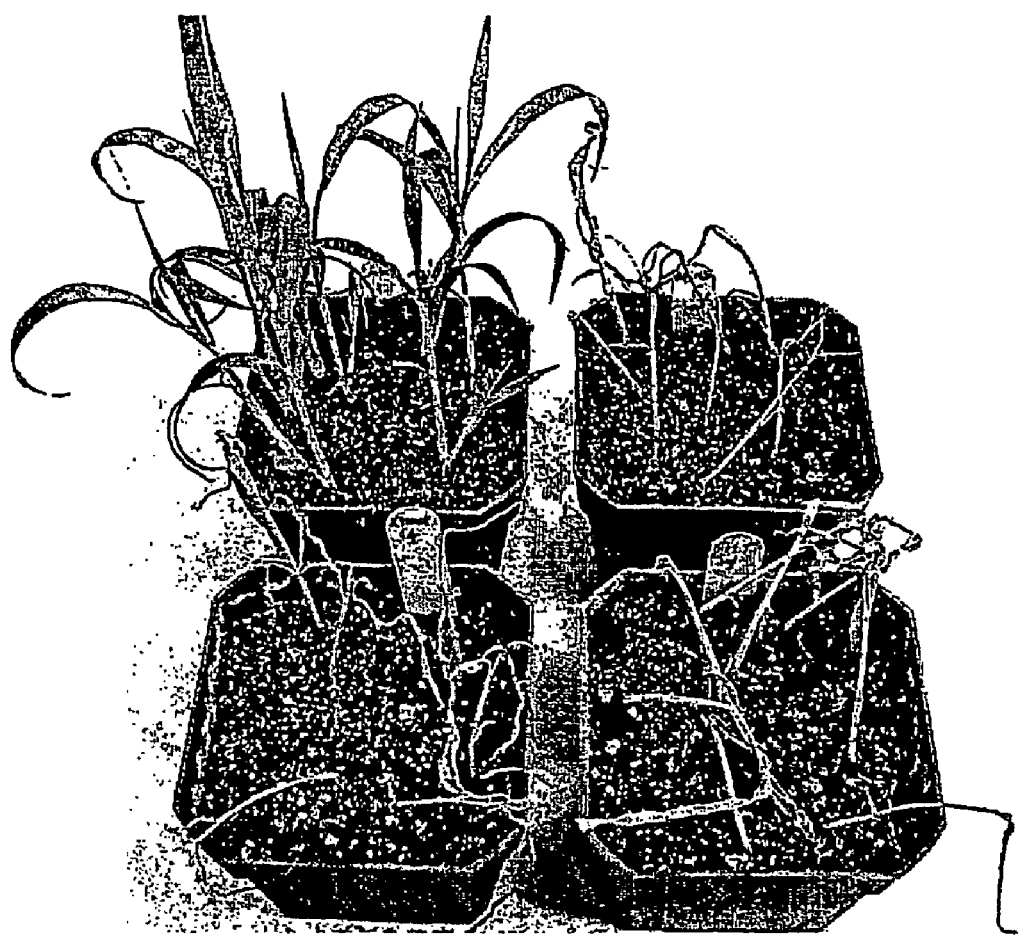
FIG. 6 shows the effect of *Pyricularia setariae* 94-409A extract on the growth of green foxtail. The plant at the top left of the figure represents the untreated green foxtail (control), the plant at the top right represents green foxtail treated with the fungal spores of 94-409A, the plant at the bottom right represents green foxtail treated with heat-treated extract of 94-409A, and the plant at the bottom left represents green foxtail treated with the regular extract of 94-409A.

Furthermore, heat-treated or non-treated extracts obtained from *Pyricularia setariae* mycelium, also result in plant death (Example 6). After 7 days following treatment with mycelial extracts, similar results were observed as that with treatments comprising extracts comprising spore inoculation (FIG. 6, and Table 7, Example 6). These results indicate that *Pyricularia setariae* produce toxic substances that exhibit weed suppressive activity. Non-sensitivity to the heat treatment suggests that the toxins are non-enzymatic in nature.

Therefore, the present invention provides an extract obtained from a biocontrol agent that exhibits weed suppressive activity, and may be used to control weed growth, for example but not limited to green foxtail.

Reduction of Application Volume by Increasing Inoculum Concentration

Figure 4:
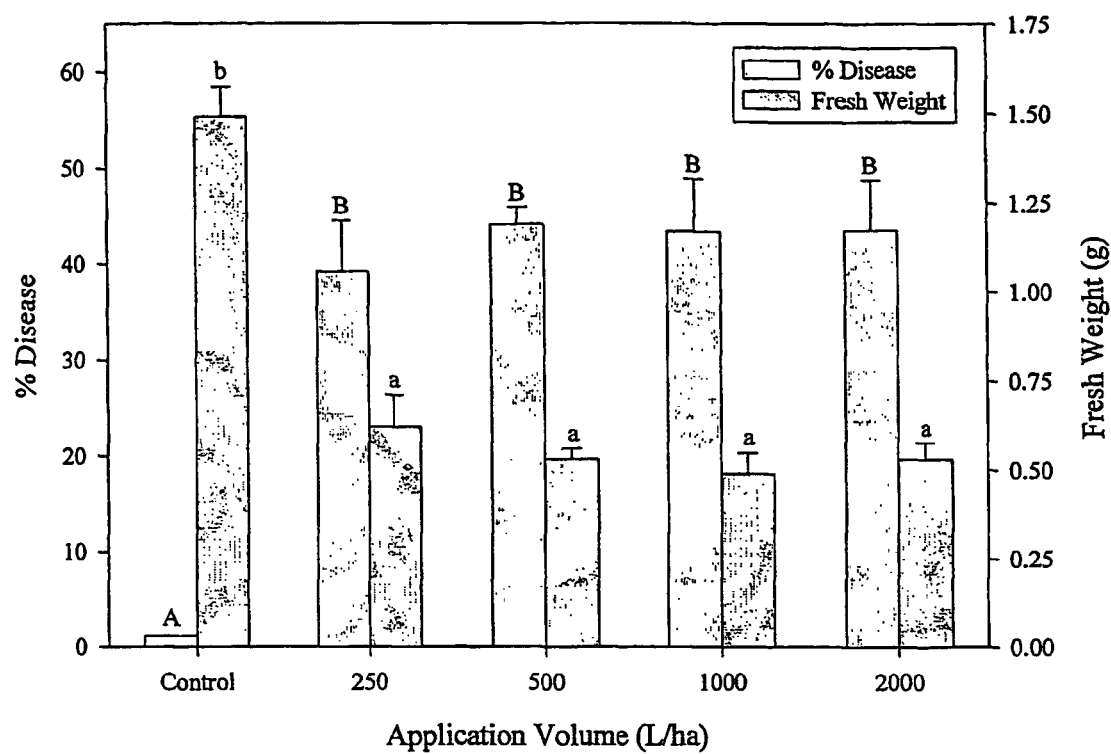
FIG. 4 shows the effect of increased concentration doses of biocontrol agent 94-409A on the efficacy of green foxtail weed control with reduced application volumes.

Referring now to FIG. 4, there is shown the effect of application dose of biocontrol agent *Pyricularia setariae*, for example 94-409A, on the fresh weight and % disease of green foxtail plants. Increasing the spore concentration of biocontrol agent 94-409A in a biocontrol composition offsets the efficacy loss that results from reduction of application volume. Further, little difference in biocontrol efficacy is observed with all the volumes applied based on the measurement of disease severity and plant fresh weight. Compared with the control, the average reduction of fresh weight ranged from about 58 to about 67% with different application volume treatments.

Thus, the use of high spore concentrations of biocontrol agent 94-409A in a biocontrol composition may reduce the application volume without compromising the efficacy of weed control. In addition, a high spore concentration increases the number of propagules contained in the spray, avoiding large numbers of 'empty' droplets.

As demonstrated in Example 3 below, biocontrol agent *Pyricularia setariae* 94-409A (IDAC) 190701-1; Jul. 19, 2001) exhibits specificity to green foxtail, and does not adversly affect a range of commercial plants thereby permitting use in an agricultural or horticultural setting. Similar results are also observed for biocontrol agents *Pyricularia setariae* 01-069A (IDAC 290102-01, Jan. 29, 2002), *Pyricularia setariae* 01-071A (IDAC 290102-02, Jan. 29, 2002), or a combination thereof. Therefore, the present invention also provides for a method of suppressing weeds during crop growth comprising spraying an effective amount of a biocontrol composition comprising biocontrol agent, *Pyricularia setariae*, for example but not limited to *Pyricularia setariae* 94-409A (IDAC 190701-1; Jul. 19, 2001), *Pyricularia setariae* 01-069A (IDAC 290102-01, Jan. 29, 2002), *Pyricularia setariae* 01-71A1(IDAC 290102-02, Jan. 29, 2002), or a combination thereof, formulated in an acceptable medium, to an area of plants, and growing the plants.

Furthermore, as indicated in Examples 11 and 12, the present invention provides a method for the for the suppression of green foxtail, and related, weeds for example but not limited to yellow and giant foxtail (*S. faberi*) by applying *Pyricularia setariae* (see Example 12, Table 14). Weed suppressive activity arising from *Pyricularia setariae*, is also observed on yellow and giant foxtail (*S. faberi*) when the biocontrol agent of the present invention is applied in combination with an herbicide, (Examples 11 and 12, Tables 12 to 14). A variety of herbicides may be used in conjunction with *Pyricularia setariae*, and include but are not limited to ACCase inhibitors, ALS inhibitors, synthetic auxins, inhibitors of photosynthesis at PSII, inhibitors of EPSP, or inhibitors of glutamine synthetase.

The above description is not intended to limit the claimed invention in any manner, furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

Materials and Methods

Preparation of Plants

Mature green foxtail seeds were harvested from a weed nursery on the research farm of Agriculture and Agri-Food Canada near Saskatoon. Seeds were planted in a layer of Redi-Earth on top of a layer of soil-less mix with fertilizer in 7.5-cm plastic pots, and grown at 20±3° C. with 14-h supplementary lighting for about 3 weeks until the 3-leaf stage.

Biological Control Agents

Three isolates of *Pyricularia setariae* were obtained; one from southwestern Ontario in 1994, and two from southeastern Saskatchewan during a 2001 field survey (Table 2).

TABLE 2

Information on different isolates of *Pyricularia setariae*

| Name | Location | site | Growth stage of weed | Disease symptoms |
|---|---|---|---|---|
| 94-409A | Chatham, ON | field crop | flowering/seed setting | leaf spot |
| 01-069A | Moosemin, SK | field crop | seed setting | leaf spot |
| 01-071A | Fairlight, SK | field crop | seed setting | leaf spot |

Inoculum Production

Mycelium plugs (5×5 mm) were cut from the edge of growing cultures of an isolate, placed on a modified oatmeal agar in petri plates, and incubated at 26° C. with 14 h of near-UV lighting. Sporulating cultures were flooded with 5 ml of sterilized water and a 0.1-ml aliquot of the suspension was plated on oatmeal agar (15 g of oatmeal flour and 12.5 g dextrose per liter water) and incubated under the same conditions for approiately 1 week. This method usually produced about $10^8$ spores/plate. A procedure has been developed for pilot-scale production using solid substrate. The protocol works for all three isolates, yielding approximately 5 billion spores per production tray (40×60 cm).

Innoculation of Plants

For inoculations, sporulating cultures were flooded with water containing 0.1% Tween 80 (surfactant) and the spores were scraped off the medium. Concentrations of spore suspensions were estimated using a haemocytometer and adjusted accordingly. An airbrush sprayer and broadcast cabinet sprayer were used to apply spore suspensions of the fungal biocontrol agents. Constant air pressure at approximately 250 kPa was used in both airbrush and broadcast spraying. Approximately 3 ml of suspension was required to achieve visible runoff for plants at the 3-4 leaf stage in a 7.5-cm-diameter pot. For broadcast application, several types of Tee-Jet nozzles according to rates and spray quality were tested. Inoculated plants were placed immediately in an environment-controlled dew chamber at 20° C.±2° C. and 20 hours dark/4 hours light prior to being placed in the green house.

Disease Assessment of Plants

Plant reactions were assessed 7 days after inoculation. The efficacy of the fungal biocontrol agent used was estimated using disease severity measured on the basis of percent diseased areas on a whole plant. A 0-11 scale adopted from Horsfall-Barratt (1945; which is herein incorporated by reference) was used to facilitate the assessment, in which scale 0 indicates no visible symptoms, 11 indicates a dead plant, and the other classes represent a range of disease severity in between The data were converted to percent disease for statistical analysis.

In addition, plants were cut at the soil line from each replicated plot and measured for fresh weight as an indicator of weed suppression. Percent fresh weight (FW) reduction [(mean control FW−treatment FW)/mean control FW×100] was calculated prior to statistical analysis.

Data Analysis

All data were subjected to analysis of variance (ANOVA) using STATISTICA 1999 software. LSD ($P \leq 0.05$) was used to separate treatment means when a significant difference ($P \leq 0.05$) was indicated in ANOVA.

EXAMPLE 1

Spray Retention Studies

Six replicated pots, each containing 8 plants at the 3-leaf stage were used for all treatments. Plants were sprayed with a Rhodamine WT dye solution containing 0.1% (v/v) Tween 80 surfactant, and the relative retention of the spray on plants was estimated by washing plant tissues in ethanol and measuring the dye amount on a spectrophotometer (Wolf et al, 2000; which is herein incorporated by reference). Measurements were taken on various plant parts, as well as on the whole plant The top, mid, and bottom leaves were cut carefully and separated from the stem. Spray retained on individual parts and whole plants was measured separately, and reported in μl dye/mg plant dry matter.

To compare spray retention on plants using different application methods and droplet sizes, an airbrush sprayer and broadcast sprayer with a series of TeeJet flat fan nozzles were used. For airbrush application, approximately 3 ml of solution was applied to a pot of plants. The application usually resulted in runoff of the spray from the plants. For broadcast application, plants were placed in a spray chamber and sprayed with various volumes. Plastic petri plates were placed beside the plants in the spray chamber to collect and determine the actual spraying volumes (Wolf et al., 1997 which is herein incorporated by reference).

Effects of Droplet Size and Travel Speed on Retention

A spray cabinet was used to identify spraying parameters for improvement of spray retention and reduction of carrier volume. Retention Efficiency was used to compare the effect of variables, in which retention on plants was measured in relation to actual application volumes determined using petri plate collection as described above. TeeJet XR 8001, 8002, and 8004 nozzles were used to create different droplet size spectra and their effect on retention was examined at travel speeds of 0.55 and 1.1 km/h.

Retention and Biocontrol Efficacy

For comparison of the biocontrol efficacy of airbrush and broadcast applications at volumes resulting in a similar level of retention on the plant. In broadcast spraying, a single XR 8004 tip or two XR 8002 tips in a Lurmark Twin Cap were used to assess the effects of droplet size and spray trajectory.

Spore suspensions of 94-409A at concentrations of $10^6$ and $10^7$ spores/ml were applied to plants. The experiment was a completely randomized factorial design with 4 replicates (pots) for each treatment.

Application Volume and Concentration Dose:

A broadcast sprayer with a single or two XR 8002 tips operated at 250 kPa was used to apply the mycoherbicide agent at approximately 250, 500, 1000, and 2,000 L/ha Carrier volume was altered by changing the sprayer travel speed between 0.28 and 1.1 km/h. Spore concentrations for the lower application volumes was increased so all treatments had the same applied fungal propagule dose. The experiment was arranged in a completely randomized design with 6 replicates for each treatment The results presented herein suggest that:

1. A broadcast spray delivering approximately 2000 L/ha provides similar spray retention amounts and biocontrol efficacy on green foxtail in comparison to an airbrush spray to the point of runoff.
2. Reductions in carrier volume may be offset by increasing spore concentration, suggesting that spore dose, not carrier volume, may govern bioherbicide efficacy.
3. Spray retention on plants may be improved by using finer sprays and angling the spray trajectory forward, backward or both forward and backward from the vertical.
4. *Pyricularia* can be used as an effective bioherbicide against weeds, for example green foxtail.

EXAMPLE 2

Efficacy of Weed Control as Foliar-Applied Agents

An experiment was conducted to compare the three isolates *Pyricularia setariae* 94-409A, 01-069A or 01-071A for control of green foxtail. All inoculations were carried out using fungal spore suspensions applied with an airbrush sprayer to achieve runoff on the foliage of the weed at the 3-4 leaf stage. The spore concentrations were adjusted to sub-lethal doses at approximately $2\text{-}3\times10^6$ spores/ml. Inoculated plants were given 24 hours dew, then placed in the greenhouse. Disease severity at whole-plant level and plant fresh weight were measured one week after inoculation to determine the efficacy of weed control.

The three isolates of *Pyricularia setariae* all caused significant damage to green foxtail, as reflected by the percentage of disease and fresh weight reduction (Table 3).

TABLE 3

Effect of *Pyricularia setariae* isolates on green foxtail

| Isolate | Disease severity (%) | Fresh weight reduction (%) |
| --- | --- | --- |
| Control | 1.17 ± 0.00* | 0.00 ± 7.17 |
| 94-409A | 72.46 ± 1.12 | 46.73 ± 9.16 |
| 01-069A | 75.83 ± 3.00 | 53.27 ± 5.15 |
| 01-071A | 77.44 ± 2.50 | 59.30 ± 2.77 |

*Mean ± standard error

Figure 5:
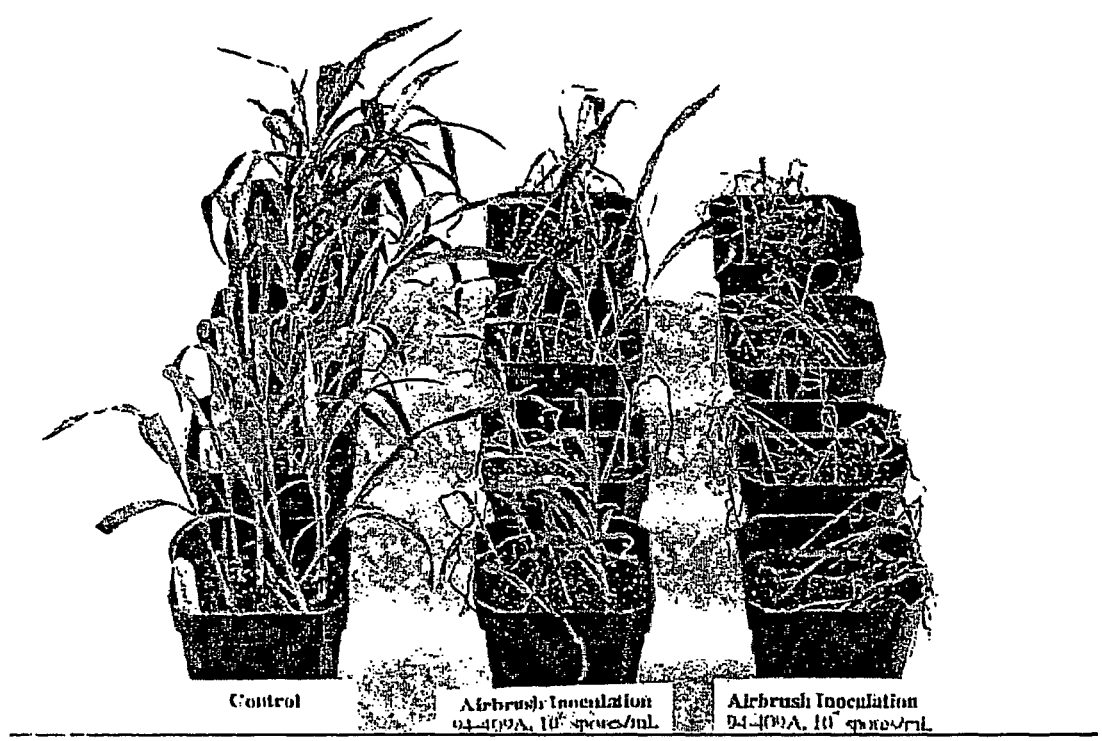
FIG. 5 shows the effect of airbrush inoculation of green foxtail with spores of *Pyricularia setariae* 94-409A, used at a concentration of $1 \times 10^6$/ml and $1 \times 10^7$/ml.

There was generally no difference in weed control efficacy among the three isolates. Without formulation, spore suspensions at $1\times10^7$/ml are more effective than those at $1\times10^6$ spores/ml (FIG. 5). The damage caused by these agents became apparent 4 days after inoculation. In comparison, most post-emergent herbicides result in symptoms 7 days after spray.

EXAMPLE 3

Crop Safety

Specificity of isolate 94-409A (IDAC 190701-1) was determined on a range of commercial cultivars using the methods outlined in Examples 1-3. All inoculations were done by airbrush spraying. Plants were given 48 hours of dew (twice as long as necessary for infection of green foxtail). Treatments: control =uninoculated plants, inoculated =plants inoculated with 94-409A spore suspensions. Disease ratings: done with the Horsfall-Barratt scale two weeks after inoculation and the data were converted to percent disease for statistical analyses. Each crop species was inoculated using 3-5 replicated pots, each containing 3 to 10 plants. The results of this experiment are present in Table 4.

TABLE 4

Reaction of common field-crop species to inoculation of *Pyricularia setariae*

| Species | Common Name | Cultivar | Treatment | Disease severity (%) | Plant reaction |
| --- | --- | --- | --- | --- | --- |
| *Setaria viridis* | Green foxtail | N/A | inoculated | 20.96 | Susceptible |
|  |  |  | control | 1.33 |  |
| *Agrostis stolonifera* | Creeping bentgrass | Unknown | inoculated | 1.17 | Immune |
|  |  |  | control | 1.17 |  |
| *Avena fatua* | Wild Oat | N/A | inoculated | 1.25 | Immune |
|  |  |  | control | 1.50 |  |
| *Avena sativa* | Oat | Walden | inoculated | 1.45 | Immune |
|  |  |  | control | 1.17 |  |
| *Brassica juncea* | Mustard | AC Vulcan | inoculated | 1.17 | Immune |
|  |  |  | control | 1.17 |  |
|  |  | Ochre | inoculated | 1.17 | Immune |
|  |  |  | control | 1.17 |  |
| *Brassica napus* | Argentine Canola | Westar | inoculated | 1.17 | Immune |
|  |  |  | control | 1.17 |  |
| *Brassica rapa* | Polish Canola | Reward | inoculated | 1.17 | Immune |
|  |  |  | control | 1.17 |  |
| *Cartamus tintorius* | Safflower | Saffric | inoculated | 1.17 | Immune |
|  |  |  | control | 1.17 |  |
| *Cicer arietinum* | Chickpea | Sanford | inoculated | 1.17 | Immune |
|  |  |  | control | 1.17 |  |
| *Festuca rubra* | Creeping red fescue | Boreal | inoculated | 1.17 | Immune |
|  |  |  | control | 1.17 |  |

TABLE 4-continued

Reaction of common field-crop species to inoculation of *Pyricularia setariae*

| Species | Common Name | Cultivar | Treatment | Disease severity (%) | Plant reaction |
|---|---|---|---|---|---|
| *Glycine max* | Soybean | Elgin 87 | inoculated | 1.17 | Immune |
| | | | control | 1.17 | |
| | | Stirling | inoculated | 1.17 | Immune |
| | | | control | 1.17 | |
| | | Williams | inoculated | 1.17 | Immune |
| | | | control | 1.17 | |
| *Helianthus annuus* | Sunflower | Cargill SF 270 | inoculated | 1.17 | Immune |
| | | | control | 1.17 | |
| *Hordeum vulgare* | Barley | CDC Silky | inoculated | 1.17 | Immune |
| | | | control | 1.17 | |
| | | Harrington | inoculated | 1.17 | Immune |
| | | | control | 1.30 | |
| *Lens culinaris* | Lentil | Estom | inoculated | 1.17 | Immune |
| | | | control | 1.17 | |
| | | Laird | inoculated | 1.17 | Immune |
| | | | control | 1.17 | |
| *Linum usitatissimum* | Flax | Linola 989 | inoculated | 1.17 | Immune |
| | | | control | 1.17 | |
| *Lolium perenne* | Perennial ryegrass | Barball | inoculated | 1.17 | Immune |
| | | | control | 1.17 | |
| *Medicago sativa* | Alfalfa | Bewar | inoculated | 1.17 | Immune |
| | | | control | 1.17 | |
| *Oryza sativa* | Rice | M202 | inoculated | 1.17 | Immune |
| | | | control | 1.17 | |
| *Panicum miliaceum* | Proso Millet | NC 22-3 | inoculated | 2.32 | Highly resistant |
| | | | control | 1.17 | |
| *Phalaris canariensis* | Canary seed | Cantate | inoculated | 1.17 | Immune |
| | | | control | 1.17 | |
| *Pisum sativum* var. *arvense* | Field pea | Express | inoculated | 1.17 | Immune |
| | | | control | 1.17 | |
| *Poa pratensis* | Kentucky bluegrass | Dormie | inoculated | 1.17 | Immune |
| | | | control | 1.17 | |
| *Sorghum bicolor* | Sorghum | Unknown | inoculated | 1.17 | Immune |
| | | | control | 1.17 | |
| *Triflium pratense* | Red Clover | Guard | inoculated | 1.17 | Immune |
| | | | control | 1.17 | |
| *Triticum aestivum* | Spring Wheat | AC Karma | inoculated | 1.37 | Immune |
| | | | control | 1.17 | |
| | Bread Wheat | AC Barrie | inoculated | 1.17 | Immune |
| | | | control | 1.17 | |
| *Triticum durum* | Durum Wheat | Kyle | inoculated | 1.17 | Immune |
| | | | control | 1.17 | |
| *Vicia faba* | Faba bean | CDC Fatima | inoculated | 1.17 | Immune |
| | | | control | 1.17 | |
| *Zea mays* | Corn | Sweet corn (unknown cv.) | inoculated | 1.17 | Immune |
| | | | control | 1.17 | |
| | | Pioneer 39K73 | inoculated | 1.17 | Immune |
| | | | control | 1.17 | |
| | | Pioneer 39M27 | inoculated | 1.96 | Highly resistant |
| | | | control | 1.17 | |
| | | Pioneer 39W54 | inoculated | 1.56 | Highly resistant |
| | | | control | 1.17 | |

As shown in Table 4, significant damage was found only on green foxtail during the observation period, 2 weeks post inoculation. These results demonstrate host specificity of the biocontrol agent of the present invention. These data suggest that *Pyricularia setariae* is safe to all field crops and turf species tested even under extremely conducive conditions provided for infection.

EXAMPLE 4

Efficacy in Pre-Emergent Applications

*Pyricularia setariae* 94-409A was evaluated for pre-emergent efficacy against green foxtail by either drenching the soil containing weed seeds or coating the seeds with a spore suspension then sowing into non-treated soils. 25 seeds were planted in a 4-inch pot, and each treatment was assigned 4 pots as replications. Emergence was assessed at 7 and 14 days after planting. Plant fresh weight was taken for each treatment 14 days after planting. Percent fresh weight reduction was calculated prior to statistical analysis. The results are shown in Table 5.

TABLE 5

Effect of 94-409A on green foxtail when applied as soil drench or seed coating.

| Treatment | % Emergence | | Fresh Weight Reduction (%) |
| | Day 7 | Day 14 | |
| --- | --- | --- | --- |
| Control | 91.00 ± 1.00* | 95.00 ± 1.91 | 0.00 ± 1.93 |
| Soil drench | 98.00 ± 1.15 | 99.00 ± 1.00 | 21.82 ± 5.59 |
| Seed coating | 59.00 ± 5.00 | 79.00 ± 1.00 | 71.45 ± 3.42 |

*Mean ± standard error

The result shown in Table 5, demonstrate that seed coating reduced emergence and plant fresh weight significantly, while soil drench appeared to be more effective in reducing fresh weight than reducing emergence. Both pre-emergent application methods have the potential to control green foxtail.

EXAMPLE 5

Efficacy of a Mycelial Formulation of 94-409A

A modified oatmeal broth (500 ml in a 1L flask) was inoculated with 5 ml of a 94-409A spore suspension and cultured on a shaker (150 rpm) at 15° C. for four weeks. The resulting mycelium was harvested by initially filtering the culture through cheesecloth (the filtrate was kept for toxin testing to be described in the following section), then washed with sterile distilled water. Ten grams of the wet mycelium was re-suspended and homogenized in 10 ml distilled water. Half of this suspension was added to 250 ml of a "Stabileze" formulation (Amsellum, et al, 1999), the other half to 250 ml distilled water.

A "Stabileze" formulation blank and a sample of 94-409A in water ($1.0 \times 10^7$ spores/ml) were also included as controls. All treatments were applied with a hand-held spray bottle, due to the viscosity of the "Stabileze" formulation. Plants were given 24 hours of dew.

Severity of disease and fresh weight reduction were estimated using the same method described above. Each treatment was applied to 6 pots of green foxtail (8 plants per pot) for replication. The results are present in Table 6.

TABLE 6

Effect of 94-409A mycelium on green foxtail

| Treatment | Disease severity (%) | Fresh Weight Reduction (%) |
| --- | --- | --- |
| Control | 1.17 ± 0.00* | 0.00 ± 9.06 |
| "Stabileze" Blank | 1.17 ± 0.00 | 4.29 ± 9.20 |
| Mycelium + "Stabileze" | 2.41 ± 0.11 | 14.73 ± 7.74 |
| Mycelium in water | 1.39 ± 0.08 | −1.81 ± 7.37 |
| Spores in water | 57.78 ± 6.25 | 68.04 ± 3.36 |

*Mean ± standard error

Although the mycelium in water could cause slight infection, the disease was more noticeable with the mycelium in "Stabileze" formulation. The symptoms caused by mycelium are similar to those caused by the spores, although the disease severity and weed-control efficacy were much lower than those caused by the spore suspension. It is likely that for mycelium to be more effective, appropriate formulations are required.

EXAMPLE 6

Effect of Secondary Metabolites of 94-409A

One liter of filtrate from the filtration of mycelium described above was concentrated by freeze-drying and re-suspending in 50 ml distilled water. One half of the extract was heated to 80° C. for 30 minutes to inactivate enzymatic substances. A 94-409A suspension containing $1.0 \times 10^7$ spores/ml and a blank medium broth were included in the experiment as checks. All applications were done using an airbrush sprayer. Plants were given 24 hours of dew. Severity of damage and fresh weight reduction were estimated using the same method described above. Each treatment consisted of 4 replicated pots of green foxtail (8 plants/pot) at the 3-4 leaf stage. The results are present in Table 7.

TABLE 7

Effect of culture-filtrate extract of 94-409A on green foxtail.

| Treatment | Disease severity (%) | Fresh Weight Reduction (%) |
| --- | --- | --- |
| Control | 1.17 ± 0.00* | 0.00 ± 7.47 |
| Broth | 1.17 ± 0.00 | −3.64 ± 6.22 |
| Extract | 97.54 ± 0.74 | 88.52 ± 1.11 |
| Heat-treated Extract | 95.60 ± 0.92 | 84.99 ± 1.02 |
| Spores | 96.63 ± 0.30 | 86.65 ± 1.00 |

*Mean ± standard error

Both heat-treated or non-treated extracts obtained from mycellium, resulted in very rapid plant death, with effects apparent 24 hours after inoculation. After 7 days, there was no difference between these treatments and the spore inoculation in terms of the level of visual damage (FIG. 6) and fresh weight reduction (Table 7). It is clear that this fungus produces toxic substances that are effective against green foxtail. Non-sensitivity to the heat treatment suggests that the toxins are non-enzymatic in nature.

EXAMPLE 7

Effect of Temperature

Germination and appressorial formation (infection structure) of 94-409A spores on leaves of green foxtail under different temperatures were rated at different time intervals (Table 8). A spore suspension was applied to 2-cm green foxtail leaf pieces laid on moist filter paper in petri dishes using an airbrush sprayer. The dishes were covered and incubated in dark at three different temperatures. 100 spores in random fields of view under light microscope were examined for each of 3 replicated leaf pieces for each temperature-time interval. The results are presented in Table 8.

TABLE 8

Germination and appressorial formation of 94-409A spores on leaves of green foxtail at different temperatures

| | 14° C. | | 20° C. | | 26° C. | |
|---|---|---|---|---|---|---|
| Time (h) | % Germination | % Appressoria | % Germination | % Appressoria | % Germination | % Appressoria |
| 0 | 0.00 ± 0.00* | 0.00 ± 0.00 | 0.00 ± 0.00 | 0.00 ± 0.00 | 0.00 ± 0.00 | 0.00 ± 0.00 |
| 2 | 22.67 ± 4.33 | 0.00 ± 0.00 | 89.67 ± 2.85 | 20.67 ± 3.71 | 84.33 ± 0.88 | 22.00 ± 5.29 |
| 4 | 70.67 ± 2.73 | 10.67 ± 1.76 | 88.33 ± 0.88 | 71.33 ± 7.33 | 94.67 ± 1.86 | 73.33 ± 6.57 |
| 6 | 75.67 ± 6.39 | 52.00 ± 10.26 | 93.00 ± 1.53 | 87.33 ± 1.76 | 91.67 ± 1.76 | 89.33 ± 7.86 |
| 8 | 85.00 ± 4.16 | 76.67 ± 2.40 | 96.67 ± 0.88 | 94.67 ± 2.67 | 97.67 ± 1.45 | 90.00 ± 3.06 |
| 12 | 94.00 ± 1.73 | 96.00 ± 1.15 | 97.67 ± 2.33 | 96.00 ± 1.15 | 96.00 ± 0.58 | 92.00 ± 7.02 |

*Mean ± standard error

In general, spores of 94-409A can germinate and produce the infection structure over a wide range of temperatures, suggesting that the biocontrol agent may be used over a wide range of temperature conditions. At 14° C., the germination and infection process can be delayed for 2 to 4 hours in comparison to those at the higher temperatures. Therefore it is possible that at lower temperatures, longer dew periods may be required for successful infection by this agent

EXAMPLE 8

Dew Requirements

All inoculations were done by airbrush spray. Inoculated plants were provided with variable dew durations at 20° C. Severity of disease and fresh weight reduction were estimated using the same method described above. Each treatment consisted of 4 replicates. Results are presented in Table 9.

TABLE 9

Control of green foxtail by 94-409A under variable leaf-wetness duration.

| Leaf | Trial 1 | | Trial 2 | |
|---|---|---|---|---|
| wetness duration | Disease severity (%) | Fresh Weight Reduction (%) | Disease severity (%) | Fresh Weight Reduction (%) |
| Control | 1.37 ± 0.11* | 0.00 ± 6.38 | 1.56 ± 0.00 | 0.00 ± 10.09 |
| 0 h | 1.17 ± 0.00 | −10.83 ± 6.85 | 1.17 ± 0.00 | −12.88 ± 10.79 |
| 6 h | 2.35 ± 0.28 | 9.17 ± 12.65 | 1.17 ± 0.00 | −12.27 ± 7.85 |
| 8 h | 45.83 ± 5.95 | 59.17 ± 2.85 | 19.14 ± 4.62 | 27.61 ± 9.89 |
| 10 h | 77.02 ± 2.46 | 75.00 ± 2.15 | 44.79 ± 5.66 | 43.56 ± 4.80 |
| 12 h | 68.30 ± 5.40 | 73.33 ± 3.60 | 47.40 ± 4.76 | 52.15 ± 4.07 |
| 24 h | 75.55 ± 7.31 | 76.67 ± 3.04 | 47.92 ± 2.08 | 48.47 ± 5.58 |

*Mean ± standard error

These results suggest that a continuous dew period of 6 to 8 hours is required for significant disease incidence. A dew period of about 10 hours resulted in the maximum level of disease, resulting in equally effective weed control compared to longer dew periods. This study suggests that non-formulated spores of 94-409A cause severe disease on green foxtail when relatively short dew periods occur with moderate temperatures. Innovations in formulation technology have the potential to decrease this requirement further, making the agent more feasible for field applications.

EXAMPLE 9

Efficacy on an Herbicide-Resistant Population of Green Foxtail

The efficacy of 94-409A was examined on a green foxtail population (UM8) with known resistance to Group-1 acetyl-CoA carboxylase (ACCase) inhibitors. This herbicide resistant (HR) population was originally identified in a field near Thornhill, Manitoba where both fenoxaprop-p-ethyl and sethoxydim products failed to control the green foxtail at recommended rates in 1990 (Heap and Morrison 1996). To ensure herbicide populations were maintained for the following experiments, seeds were increased in the greenhouse by treating plants with the herbicide Poast Ultra EC (450 g of sethoxydim/L, BASF) at 2×label rates at the 3-leaf stage.

Plants of HR and herbicide-sensitive (HS) green foxtail were treated with either 94-409A ($1 \times 10^7$ spores/ml) or Poast Ultra EC at label rates (0.32 L/ha) using a cabinet sprayer and a flat fan TEEJET® XR8002 nozzle at a carrier volume of 200 L/ha. Control and *Pyricularia setariae*-treated plants were placed in a dew chamber for 24 h, whereas the plants treated with the herbicide were placed directly into the greenhouse. Results including the severity of damage of % fresh weight reduction were rated similarly as described above. The results are presented in Table 10.

TABLE 10

Effect of *Pyricularia setariae* (94-409A) and Poast Ultra on herbicide-resistant and susceptible populations of green foxtail.

| | Herbicide resistant green foxtail | | Herbicide susceptible green foxtail | |
|---|---|---|---|---|
| Treatment | Damage severity (%) | Fresh weight reduction (%) | Damage severity (%) | Fresh weight reduction (%) |
| Control | 3.11 ± 1.86* | 0.00 ± 5.64 | 1.27 ± 0.06 | 0.00 ± 3.46 |
| Poast Ultra | 18.50 ± 3.17 | 16.87 ± 7.50 | 72.27 ± 3.08 | 75.75 ± 1.65 |
| 94-409A | 81.85 ± 2.81 | 78.49 ± 1.86 | 76.75 ± 2.58 | 78.70 ± 1.41 |

*Mean ± standard error

The results in Table 10 demonstrate that weed control in the herbicide susceptible population was the same for herbicide and *Pyricularia setariae* treatments. However, with the herbicide resistant population, *Pyricularia setariae* was much more effective than herbicide in exhibiting weed supressive activity. In the presence of *Pyricularia setariae* the fresh weight of the herbicide resistant population of green foxtail was reduced by approximately 79% in comparison to the control, as opposed to a 17% reduction observed using the herbicide. This finding demonstrates that the biocontrol agent of the present invention has the potential to be used as a new tool for managing herbicide-resistant weed populations.

EXAMPLE 10

Compatibility of 94-409A with Herbicides in "Tank Mixtures"

Example herbicides comprising a range of herbicide groups and mechanisms of action were used at suggested label rates. Herbicides with Group Site of Action Family Active Ingredient of Group 1 (ACC-ase inhibitor) Group 2 (ALS inhibitors), Group 4 (Synthetic auxins), Group 5 (Inhibition of photosynthesis at PSII), Group 6 (PSII inhibitor, different binding behavior than Nitriles), Group 9 (Inhibition of EPSP), and Group 10 (Inhibition of glutamine synthetase) were tested.

Several common surfactants were also tested at rates based on herbicide label recommendations. Spores obtained from *Pyricularia setaria* 94-409A were suspended in herbicide solutions at room temperature for 30 minutes, then aliquots of each suspension were spread on 3 water agar plates to allow for spore germination. Percent germination was counted after 4 hours, and expressed as % of the control (% germinated spores in water). Results from this experiment are present in Table 11.

TABLE 11

Compatibility of 94-409A spores with common herbicides and surfactants

| Product | Herbicide group | Germination (as % of control) | Compatibility (Yes/No) |
|---|---|---|---|
| Achieve | 1 | 97.47 ± 8.08* | Yes |
| Assure II | 1 | 0.00 ± 0.00 | No |
| Hoegrass 284 | 1 | 3.16 ± 1.67 | No |
| Horizon | 1 | 0.00 ± 0.00 | No |
| Poast Ultra | 1 | 0.00 ± 0.00 | No |
| Select | 1 | 11.39 ± 3.29 | No |
| Ally | 2 | 100.00 ± 9.13 | Yes |
| Pursuit | 2 | 90.51 ± 6.70 | Yes |
| 2-4 D Ester | 4 | 0.00 ± 0.00 | No |
| Banvel | 4 | 91.77 ± 7.70 | Yes |
| Lontrel | 4 | 102.53 ± 2.19 | Yes |
| MCPA Na | 4 | 84.18 ± 9.32 | Yes |
| Sencor | 5 | 55.70 ± 7.46 | Possibly Yes# |
| Velpar | 5 | 92.41 ± 3.35 | Yes |
| Basagran | 6 | 106.33 ± 1.10 | Yes |
| Pardner | 6 | 1.90 ± 1.10 | No |
| Round-up | 9 | 83.54 ± 13.74 | Yes |
| Liberty | 10 | 0.00 ± 0.00 | No |
| Agral 90 | Surfactant | 0.00 ± 0.00 | No |
| Assist | Surfactant | 89.87 ± 9.13 | Yes |
| Merge | Surfactant | 63.29 ± 10.82 | Possibly Yes |
| Rely | Surfactant | 0.00 ± 0.00 | No |
| Score | Surfactant | 0.00 ± 0.00 | No |
| Turbocharge | Surfactant | 65.82 ± 3.16 | Possibly Yes* |

*Mean ± standard error
May have less impact at lower chemical concentrations.

A range of herbicides and surfactants are compatible with the biocontrol agent of the present invention, in that they do not negatively effect spore germination, a key indicator of viability and potential of effectivity of the fungus. The compatible herbicides included products from different groups, indicating the potential for tank mixes of *Pyricularia setaria* with many types of herbicide for control of multiple weed species. Use of herbicides at a lower concentration may result in compatibility with a greater number of herbicides. This is supported in Example 11, where non-compatible herbicides are used in conjuction with *Pyricularia setaria* and synergytic effects in control weed growth are observed.

EXAMPLE 11

Synergy of 94-409A with Herbicides in Controlling Green Foxtail

Selected herbicides were applied to green foxtail plants at the 5-6 leaf stage, at $1/10^{th}$ label rates using, a broadcast sprayer with an application volume of 100 L/ha. Surfactants were added as per label recommendation. Reduced herbicide rates were used to cause sub-lethal damage on the weed to facilitate determination of the nature of chemical/fungus interactions. Plants were placed in the greenhouse for 48 hours after herbicide treatment, then inoculated with 94-409A (with $2 \times 10^7$ spores/ml) at 200 L/ha. The inoculated plants were given 24 hours dew prior to being placed in the greenhouse. The severity of damage was estimated as described above. Plant fresh weight (FW) was measured 7 days after inoculation and converted into a "percent-of-control" value (% CFW) with the following equation:

$$\% \text{ CFW} = \text{treatment FW/mean control FW} \times 100$$

As opposed to fresh weight reduction used in other examples, the lower the value of % CFW, the more effective the treatment.

The nature of chemical/fungus interaction was analyzed using % CFW of each treatment following the method described by Colby (1966). Using this method, the probability of synergy is estimated by comparing actual achieved % CFW with the expected values calculated with the following equation:

$$\text{Expected}_{\% \ CFW} = \text{Herbicide}_{\% \ CFW} \times \text{Fungus}_{\% \ CFW} / 100$$

Figure 7A:
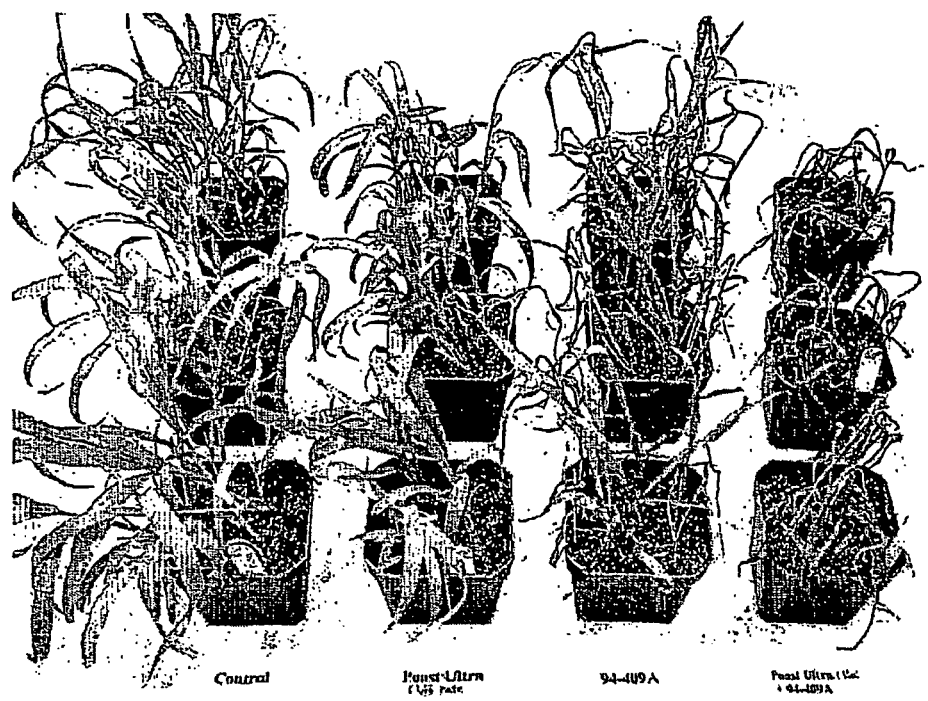
FIG. 7A shows the synergistic effect of 94-409A with the herbicide Poast Ultra.
Figure 7B:
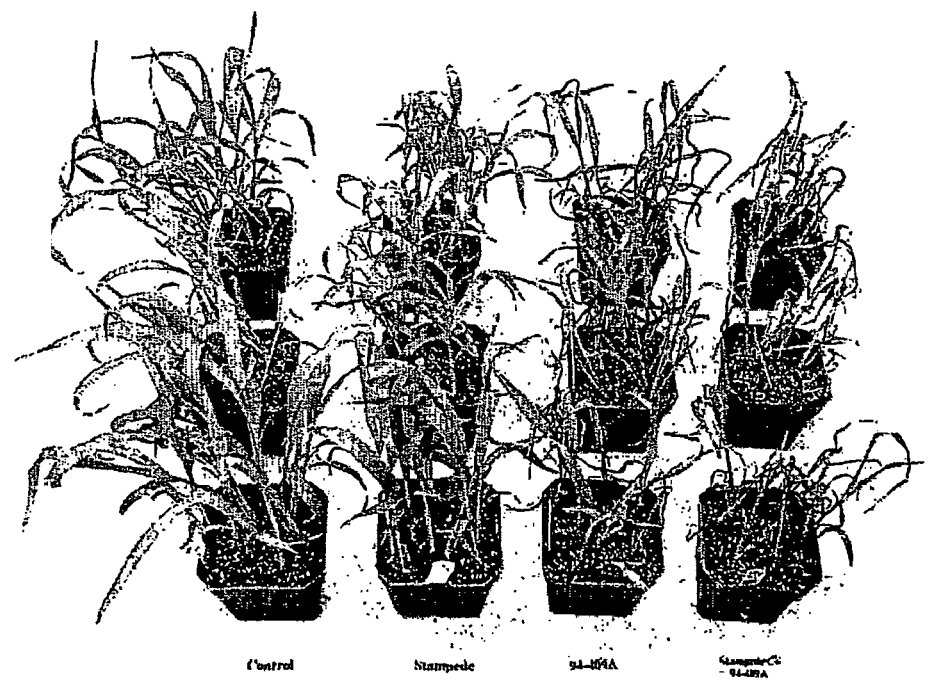
FIG. 7B shows the synergistic effect of 94-409A with the herbicide Stampede.

The greater the difference between the actual % CFW and the expected value of the combined herbicide/fungus treatment, the more synergistic the interaction. The result of these experiments are shown in Table 12 and FIG. 7.

TABLE 12

The nature of herbicide/fungus interaction on control of green foxtail

| Herbicide | Expected % CFW | Actual % CFW | Difference | Synergy |
|---|---|---|---|---|
| Accord | 44.92 | 37.85 | 7.06 | Yes |
| Achieve | 37.42 | 37.33 | 0.09 | No |
| Liberty | 39.24 | 32.91 | 6.32 | Yes |
| MCPA Na | 43.20 | 39.33 | 3.88 | No |
| Pursuit | 37.96 | 31.34 | 6.63 | Yes |
| Poast Ultra | 21.06 | 15.35 | 5.71 | Yes |
| Round-up | 43.35 | 37.33 | 6.02 | Yes |
| Stampede | 33.90 | 25.76 | 8.13 | Yes |

Most of the herbicides tested in Table 12 appeared to be synergistic when combined with *Pyricularia setaria* 94-409A. The synergy may be enhanced further by increasing chemical rates since most herbicides caused only minor injury to the plants at $1/10^{th}$ rates.

Several herbicides that were identified as being non-compatible with 94-409A in Table 11, for example, Post Ultra and Liberty, exhibit synergystic activity with 94-409A at lower concentration as indicted in Table 12. This demonstrates that a wide range of herbicides may be used in combination with *Pyricularia setaria* for the control of weed plants.

In cases where herbicides exhibited higher effectivity, the combinations with *Pyricularia setaria* caused more dramatic damage to the weed (FIG. 7), resulting in much enhanced efficacy measured by fresh weight (Table 13).

TABLE 13

Effect of co-application of herbicides and 94-409A on control of green foxtail

| Herbicide | Treatment | Disease severity (%) | % CFW |
|---|---|---|---|
| Accord | Herbicide | 1.56 ± 0.26* | 96.42 ± 13.52 |
|  | Plus Fungus | 62.55 ± 7.51 | 37.85 ± 8.56 |
| Achieve | Herbicide | 1.90 ± 0.22 | 80.34 ± 8.75 |
|  | Plus Fungus | 51.67 ± 3.96 | 37.33 ± 4.61 |
| Liberty | Herbicide | 4.54 ± 0.47 | 84.23 ± 7.17 |
|  | Plus Fungus | 55.55 ± 1.41 | 32.91 ± 2.16 |
| MCPA Na | Herbicide | 1.66 ± 0.13 | 92.74 ± 6.48 |
|  | Plus Fungus | 51.05 ± 5.22 | 39.33 ± 5.60 |
| None | Herbicide | 1.17 ± 0.00 | 100.00 ± 18.77 |
|  | Plus Fungus | 46.77 ± 2.83 | 46.58 ± 7.41 |
| Poast Ultra | Herbicide | 7.91 ± 2.46 | 45.22 ± 3.64 |
|  | Plus Fungus | 98.14 ± 0.18 | 15.35 ± 1.63 |
| Pursuit | Herbicide | 1.76 ± 0.15 | 81.49 ± 9.78 |
|  | Plus Fungus | 59.64 ± 1.82 | 31.34 ± 5.27 |
| Round-up | Herbicide | 1.46 ± 0.17 | 93.06 ± 4.17 |
|  | Plus Fungus | 53.44 ± 2.19 | 37.33 ± 2.38 |
| Stampede | Herbicide | 2.68 ± 0.49 | 72.77 ± 7.23 |
|  | Plus Fungus | 85.59 ± 0.52 | 25.76 ± 3.03 |

*Mean ± standard error

The results in Table 13 demonstrate that there is strong potential for a combined application of *Pyricularia setaria* and an herbicide to improve weed control, especially for herbicide-resistant green foxtail populations. The synergy also has potential to widen the application window for post-emergent applications, as well as improving the efficacy of the fungus on related foxtail species such as yellow and giant foxtail (*S. faberi*).

EXAMPLE 12

Efficacy on Yellow and Giant Foxtail (*S. faberi*)

Spore suspensions of 94-409A were applied to yellow and giant foxtail (*S. faberi*) (*Setaria glauca* and *S. faberi*) at the 3-4 leaf stage with an airbrush sprayer, and the plants were given 24 hours of dew immediately after inoculation. A further study was conducted by applying five groups of herbicides to yellow and giant foxtail (*S. faberi*) 36 h prior to inoculation with the fungus. The purpose of this study was to determine whether the infection could be enhanced through predisposition of the weeds with chemicals and, whether *Pyricularia setaria* would interact synergistically with any of the herbicides, resulting in improved weed control. To facilitate the assessment, herbicides were applied at a half or a quarter (sublethal) rates. Results of these experiments are given in Table 14.

TABLE 14

Interactions of *Pyricularia setaria* 94-409A with selected herbicides on yellow (Y) and giant (G) foxtail

| Treatment | Fresh weight (as % of CK) | | Expected* (as % of CK) | | Difference (%) | | Synergy determination | |
|---|---|---|---|---|---|---|---|---|
|  | Y. Foxtail | G. foxtail | Y. Foxtail | G. foxtail | Y. Foxtail | G. foxtail | Y. Foxtail | G. foxtail |
| Control (CK) | 100 | 100 |  |  |  |  |  |  |
| P. setaria (94-409A) | 79.9 | 58.4 |  |  |  |  |  |  |
| Accord | 74.9 | 53.2 |  |  |  |  |  |  |
| Accord + P. setaria | 43.0 | 39.0 | 59.8 | 31.1 | 16.8# | −7.9 | Yes | No |
| Pursuit | 17.0 | 28.6 |  |  |  |  |  |  |
| Pursuit + P. setaria | 15.0 | 22.1 | 13.6 | 16.7 | −6.0 | −5.4 | No | No |
| Poast Ultra | 22.0 | 26.0 |  |  |  |  |  |  |
| Poast Ultra + P. setaria | 10.0 | 10.4 | 17.6 | 15.2 | 7.6 | 4.8 | Yes | No |
| Round-up | 79.9 | 107.8 |  |  |  |  |  |  |
| Round-up + P. setaria | 70.9 | 51.9 | 63.8 | 63.0 | −7.1 | 11.1 | No | Yes |
| Stampede | 30.0 | 37.7 |  |  |  |  |  |  |
| Stampede + P. setaria | 30.0 | 10.4 | 24.0 | 22.0 | −1.4 | 11.6 | No | Yes |

*Expected maximum fresh weight as % of controls when synergistic interaction occurs.
Differences larger than 5.0 are considered to be positive synergy.

*P. setaria* 94-409A was capable of infecting both yellow and giant foxtail (*S. faberi*), causing visible disease symptoms on leaves. However, the severity of damage was relatively lower than that on green foxtail.

It is clear that several herbicides can significantly enhance the infection and disease due to *Pyricularia setaria* on yellow and giant foxtail (*S. faberi*). Treatment of a weed with these herbicides resulted in visible plant stunting and chlorosis on emerging leaves. The severity of weed damage was increased significantly by treating with *Pyricularia setaria* and herbicides. Analyses of plant fresh weight suggest that 94-409A is synergistic with quinclorac (Accord) and sethoxydim (Poast Ultra) in controlling yellow foxtail (*S. glauca*) and, with propanil (Stampede) and glyphosate (Roundup) on giant foxtail (*S. faberi*) (Table 14).

All citations are herein incorporated by reference.

The present invention has been described with regard to preferred embodiments. However, it will be obvious to persons skilled in the art that a number of variations and modifications can be made without departing from the scope of the invention described herein.

REFERENCES

Filippi, M. C. and Prabhu, A. S. 1998. Relationship between panicle blast severity and mineral nutrient content of plant tissue in upland rice. J. Pl Nutr. 21: 1577-78.

Graham-Bryce, I. J. 1977. Crop Protection: a consideration of the effectiveness and disadvantages of current methods and scope for improvement. *Phil. Trans. Roy. Soc. of Britain.* 281: 163-179.

Greaves, M. P., Duton, L. and Lawrie, J. 2000. Formulation of microbial herbicides. *Aspects of Applied Biology* 57 (Pesticide Application): 171-178.

Green, S. and Bailey K. L. 2000. Effects of leaf maturity, infection site, and application rate of *Alternaria cirsinoxia* conidia on infection of Canada thistle (*Cirsium arvense*). *Biological Control* 19: 167-174.

Grover, R., Caldwell, B. C., Maybank, J, and Wolf, T. M. 1997. Airborne off-target losses and ground deposition characteristics from a Spra-Coupe using 'low drift' nozzle tips. *Can. J. Plant Sci.* 77:493-500.

Hartley, G. S. and R. T. Brunskill. 1958. Reflection of water drops from surfaces. Pages 214-223 In: Surface Phenomena in Chemistry and Biology J. F. Danielli, et al. eds. Pergannon Press, London.

Himel, C. M., Loats, H. and Bailey, G. W. 1990. Pesticide sources to the soil and principles of spray physics. In: *Pesticides in the Soil Environment, Impact and Modeling*. Soil Science of America Book Series 2 (ed. H. H. Cheng), pp7-50. Soil Sci. Soc. of Am., Wisconsin.

Horsfall, J. G. and Barratt, R. W. 1945. An improved grading system for measuring plant diseases. *Phytopathology* 35:665 (Abstr.).

Jones, K. A. 1994. Use of baculoviruses for cotton pest control. In: *Insect Pest of Cotton* (eds. G. A. Matthews and J. P. Tunstall), pp. 477-504. CAB International, Wallingford, UK.

Jones, K. A. 1998. Spray application criteria. In: *Formulation of Microbial Biopesticides* (ed H. D. Burges), pp. 367-375. Academic Press, London.

Jones, K. A and Burges, H. D. 1998. Technology of formulation and application. In: *Formulation of Microbial Biopesticides*, pp. 7-30.

Knoche, M. 1994. Effect of droplet size and carrier volume on performance of foliage-applied herbicides. Crop Prot. 13:163-178.

Matthews, G. A. 1992. *Pesticide Application Methods, 2$^{nd}$ edition*. Longmnan Scientific and Technical, Harlow, UK.

Nordbo, E., K. Kristensen, and E. Kirknel. 1993. Effects of wind direction, wind speed and travel speed on spray deposition. Pestic. Sci. 38:3341.

Reichard, D. L. 1988. Drop formation and impaction of the plant. Weed Technol. 2:82-87.

Richardson, R. G. 1987. Effect of drop trajectory on spray deposits on crop and weeds. Plant Prot. Quarterly 2:108-111.

Smith, D. B. and Bouse, L. F. 1981. Machinery and factors that affect the application of pathogens. In: *Microbial Control of Pest and Plant Diseases*, pp. 635-653.

Spillman, J. J. 1984. Spray impaction, retention and adhesion: an introduction to basic characteristics. Pestic. Sci. 15:97-106.

Wolf, T. M., Liu, S. H., Caldwell, B. C., and Hsiao, A. I. 1997. Calibration of greenhouse spray chambers—the importance of dynamic nozzle patternation. *Weed Technol.* 11:428-435.

Wolf, T. M., Harrison, S. K, and Hall, F. R. 2000. Optimizing postemergence herbicide deposition and efficacy through application variables in no-till. *Weed Science* 48:761-768.

Amsellem, Z., Zidack, N. K., Quimby, P. C. Jr., and Gressel, J. 1999. Long-term dry preservation of viable mycelia of two mycoherbicidal organisms. *Crop Protection* 18:643-649.

Colby, S. R. 1966. Calculating synergistic and antagonistic responses of herbicide combinations. *Weeds* 14:20-22.

The invention claimed is:

1. An isolated fungal biocontrol agent selected from the group consisting of *Pyricularia setariae* 94-409A, deposited as IDAC 190701-1; *Pyricularia setariae* 01-069A, deposited as IDAC 290102-01; and *Pyricularia setariae* 01-071 A, deposited as IDAC 290102-02.

2. The biocontrol agent of claim 1, wherein the biocontrol agent is *Pyricularia setariae* 94-409A, deposited as IDAC 190701-1.

3. The biocontrol agent of claim 1, wherein the biocontrol agent is *Pyricularia setariae* 01-069A, deposited as IDAC 290102-01.

4. The biocontrol agent of claim 1, wherein the biocontrol agent is *Pyricularia setariae* 01-071A, deposited as IDAC 290102-02.

5. A method for suppressing weed growth comprising applying the isolated biocontrol agent of claim 1 to a foxtail weed.

6. The method of claim 5, wherein the foxtail weed is green foxtail (*Setaria viridis* [L.] Beauv.), yellow foxtail (*S. glauca*) or giant foxtail (*S. faberi*).

7. The method of claim 5, wherein the foxtail weed is green foxtail (*Setaria viridis* [L.] Beauv.).

8. A biocontrol composition comprising i) at least one isolated fungal biocontrol agent selected from the group consisting of *Pyricularia setariae* 94-409A, deposited as IDAC 190701-1; *Pyricularia setariae* 01-069A, deposited as IDAC 290102-01; and *Pyricularia setariae* 01-071A, deposited as IDAC 290102-02; and a mixture thereof, and ii) a suitable medium.

9. The composition of claim 8, wherein the at least one agent is present in an amount of about $10^6$ to about $10^7$ spores per ml.

10. The composition of claim 8, wherein the suitable medium is a liquid culture medium, a solid culture medium or a combination thereof.

11. The composition of claim 8, wherein the suitable medium is a liquid culture medium.

12. A method for suppressing weed growth comprising applying the composition of claim 8 to a foxtail weed.

13. The method of claim 12, wherein the foxtail weed is green foxtail (*Setaria viridis* [L.] Beauv.), yellow foxtail (*S. glauca*), or giant foxtail (*S. faberi*).

14. The method of claim 12, wherein the foxtail weed is green foxtail (*Setaria viridis* [L.] Beauv.).

15. The method of claim 12, wherein the composition is applied by spraying.

16. The method of claim 15, wherein said spraying comprises airbrush or broadcast spraying.

17. The method of claim 16, wherein said broadcast spraying is performed with a nozzle which produces spray droplets having a volume median diameter at 1 bar of between about 280 to about 390 microns.

18. A biocontrol composition comprising i) at least one isolated fungal biocontrol agent selected from the group consisting of *Pyricularia setariae* 94-409A, deposited as IDAC 190701-1; *Pyricularia setariae* 01-069A, deposited as IDAC 290102-01; and *Pyricularia setariae* 01-071A, deposited as IDAC 290102-02; and a mixture thereof, and ii) an herbicide.

19. The composition of claim 18, wherein the agent is present in an amount of about $10^6$ to about $10^7$ spores per ml.

20. The composition of claim 18, which further comprises a suitable medium.

21. The composition of claim 20, wherein the suitable medium is a liquid culture medium, a solid culture medium or a combination thereof.

22. The composition of claim 20, wherein the suitable medium is a liquid culture medium.

23. A method for suppressing weed growth comprising applying the composition of claim 18 to a foxtail weed.

24. The method of claim 23, wherein the foxtail weed is green foxtail (*Setaria viridis* [L.] Beauv.), yellow foxtail (*S. glauca*) or giant foxtail (*S. faberi*).

25. The method of claim 23, wherein the foxtail weed is green foxtail (*Setaria viridis* [L.] Beauv.).

26. The method of claim 23, wherein the composition is applied by spraying.

27. The method of claim 26, wherein said spraying comprises airbrush or broadcast spraying.

28. The method of claim 27, wherein said broadcast spraying is performed with a nozzle which produces spray droplets having a volume median diameter at 1 bar of between about 280 to about 390 microns.

29. A method of suppressing foxtail weed during crop growth comprising:
   a) adding to soil an effective amount of a biocontrol composition comprising at least one isolated fungal biocontrol agent selected from the group consisting of *Pyricularia setariae* 94-409A (IDAC 190701-1), *Pyricularia setariae* 01-069A (IDAC 290102-01), *Pyricularia setariae* 01-071A (IDAC 290102-02), and a mixture thereof, formulated in an acceptable medium, to produce a treated soil;
   b) planting crops in said treated soil; and
   c) growing said crops.

30. The method of claim 29, wherein the foxtail weed is green foxtail (*Setaria viridis* [L.] Beauv.), yellow foxtail (*S. glauca*) or giant foxtail (*S. faberi*).

31. The method of claim 29, wherein the foxtail weed is green foxtail (*Setaria viridis* [L.] Beauv.).

32. A method of suppressing foxtail weed during crop growth comprising:
   a) adding to soil an effective amount of a biocontrol composition comprising:
      (i) at least one fungal biocontrol agent selected from the group consisting of *Pyricularia setariae* 94-409A (IDAC 190701-1), *Pyricularia setariae* 01-069A (IDAC 290102-01), *Pyricularia setariae* 01-071A (IDAC 290102-02), and a mixture thereof; and
      (ii) an herbicide; formulated in an acceptable medium, to produce a treated soil;
   b) planting crops in said treated soil; and
   c) growing said crops.

33. The method of claim 32, wherein the foxtail weed is green foxtail (*Setaria viridis* [L.] Beauv.), yellow foxtail (*S. glauca*) or giant foxtail (*S. faberi*).

34. The method of claim 32, wherein the foxtail weed is green foxtail (*Setaria viridis* [L.] Beauv.).

35. A method of suppressing foxtail weed during crop growth, comprising:
   a) spraying an area of plants with an effective amount of a biocontrol composition comprising at least one isolated fungal biocontrol agent selected from the group consisting of *Pyricularia setariae* 94-409A (IDAC 190701-1), *Pyricularia setariae* 01-069A (IDAC 290102-01), *Pyricularia setariae* 01-071A (IDAC 290102-02), and a mixture thereof, formulated in an acceptable medium; and
   b) growing said plants.

36. The method of claim 35, wherein the foxtail weed is green foxtail (*Setaria viridis* [L.] Beauv.), yellow foxtail (*S. glauca*) or giant foxtail (*S. faberi*).

37. The method of claim 35, wherein the foxtail weed is green foxtail (*Setaria viridis* [L.] Beauv.).

38. The method of claim 35, wherein said spraying comprises airbrush or broadcast spraying.

39. The method of claim 38, wherein said broadcast spraying is performed with a nozzle which produces spray droplets having a volume median diameter at 1 bar of between about 280 to about 390 microns.

40. A method of suppressing foxtail weed during crop growth comprising:
   a) spraying an area of plants with an effective amount of a biocontrol composition comprising:
      (i) at least one fungal biocontrol agent selected from the group consisting of *Pyricularia setariae* 94-409A (IDAC 190701-1), *Pyricularia setariae* 01-069A (IDAC 29010201), *Pyricularia setariae* 01-071A (IDAC 290102-02), and a mixture thereof, and
      (ii) an herbicide, formulated in an acceptable medium; and
   b) growing said plants.

41. The method of claim 40, wherein the foxtail weed is green foxtail (*Setaria viridis* [L.] Beauv.), yellow foxtail (*S. glauca*) or giant foxtail (*S. faberi*).

42. The method of claim 40, wherein the foxtail weed is green foxtail (*Setaria viridis* [L.] Beauv.).

43. The method of claim 40, wherein said spraying comprises airbrush or broadcast spraying.

44. The method of claim 43, wherein said broadcast spraying is performed with a nozzle which produces spray droplets having a volume median diameter at 1 bar of between about 280 to about 390 microns.

45. A method of inhibiting foxtail weed in a desired area, said method comprising spraying said desired area with between about 250 L/Ha to about 2000 L/Ha of a biocontrol composition comprising between about $10^6$ to about $10^7$ spores of at least one isolated fungal biocontrol agent selected from the group consisting of *Pyricularia setariae* 94-409A (IDAC 190701-1), *Pyricularia setariae* (01-069A (IDAC 29010201), *Pyricularia setariae* 01-071A (IDAC 290102-02), and a mixture thereof.

46. The method of claim 45, wherein the foxtail weed is green foxtail (*Setaria viridis* [L.] Beauv.), yellow foxtail (*S. glauca*) or giant foxtail (*S. faberi*).

47. The method of claim 45, wherein the foxtail weed is green foxtail (*Setaria viridis* [L.] Beauv.).

48. The method of claim 45, wherein said spraying comprises airbrush or broadcast spraying.

49. The method of claim 48, wherein said broadcast spraying is performed with a nozzle which produces spray droplets having a volume median diameter (VMD) at 1 bar of between about 280 to about 390 microns.

* * * * *